US010386354B2

(12) United States Patent
Radjy

(10) Patent No.: US 10,386,354 B2
(45) Date of Patent: Aug. 20, 2019

(54) SENSING DEVICE, SENSING DEVICE SYSTEM, AND METHODS FOR MEASURING A CHARACTERISTIC OF A CONCRETE MIXTURE AND FOR PREDICTING A PERFORMANCE CHARACTERISTIC OF A CONCRETE MIXTURE

(71) Applicant: QUIPIP, LLC, Pittsburgh, PA (US)

(72) Inventor: Farrokh F. Radjy, Pittsburgh, PA (US)

(73) Assignee: QUIPIP, LLC, Pittsburgh, PA (US)

( * ) Notice: Subject to any disclaimer, the term of this patent is extended or adjusted under 35 U.S.C. 154(b) by 0 days.

(21) Appl. No.: 15/420,635

(22) Filed: Jan. 31, 2017

(65) Prior Publication Data
US 2017/0219553 A1    Aug. 3, 2017

Related U.S. Application Data

(60) Provisional application No. 62/356,378, filed on Jun. 29, 2016, provisional application No. 62/343,635, filed on May 31, 2016, provisional application No. 62/289,723, filed on Feb. 1, 2016.

(51) Int. Cl.
G01N 33/38    (2006.01)
G01N 25/00    (2006.01)

(52) U.S. Cl.
CPC ........... *G01N 33/383* (2013.01); *G01N 25/00* (2013.01)

(58) Field of Classification Search
CPC .............................. G01N 33/383; G01N 25/00
See application file for complete search history.

(56) References Cited

U.S. PATENT DOCUMENTS

| 5,082,371 | A | 1/1992 | Ansari |
| 6,334,707 | B1 * | 1/2002 | Ku .......................... G01K 1/143 374/147 |
| 6,798,220 | B1 | 9/2004 | Flanigan |
| 8,966,982 | B2 | 3/2015 | Liu et al. |
| 2002/0031165 | A1 | 3/2002 | Zollinger et al. |
| 2002/0041621 | A1 * | 4/2002 | Faries, Jr. ............... A61M 5/14 374/147 |
| 2007/0065071 | A1 | 3/2007 | Slade et al. |
| 2011/0094295 | A1 | 4/2011 | Meadows et al. |
| 2011/0120576 | A1 | 5/2011 | Sigouin et al. |

(Continued)

FOREIGN PATENT DOCUMENTS

CA    2155471 A1    2/1997

OTHER PUBLICATIONS

NRMCA ("Concrete in Practice", by NRMCA, published in 2001, see attached publication).*

(Continued)

*Primary Examiner* — Xin Y Zhong
(74) *Attorney, Agent, or Firm* — Lucas & Mercanti, LLP

(57) ABSTRACT

A sensing device includes a concave side adapted to conform to a curvature of an outer side of a standard concrete test cylinder, a temperature sensor, and a humidity sensor. In one embodiment, the sensing device includes a capillary needle disposed on the concave side. The capillary needle comprises a humidity sensor. The sensing device is attached to the side of a concrete test cylinder, temperature and humidity measurements are obtained by the sensing device, and a prediction of maturity and strength of the concrete is generated based on the temperature and humidity measurements.

6 Claims, 31 Drawing Sheets

(56) References Cited

U.S. PATENT DOCUMENTS

| | | |
|---|---|---|
| 2013/0343734 A1 | 12/2013 | Dock, II |
| 2014/0007695 A1* | 1/2014 | Darbe .................. G01N 3/10 73/803 |
| 2014/0216143 A1* | 8/2014 | Salmi .................. G01N 19/10 73/73 |
| 2015/0068523 A1 | 3/2015 | Powers et al. |
| 2015/0212061 A1 | 7/2015 | Radjy |
| 2015/0315078 A1 | 11/2015 | Feldman et al. |
| 2015/0355160 A1 | 12/2015 | Berman |
| 2016/0018383 A1 | 1/2016 | Radjy |
| 2016/0223512 A1* | 8/2016 | Radjy ................ G01N 25/20 |

OTHER PUBLICATIONS

International Search Report dated Apr. 4, 2017 from corresponding to International Application No. PCT/US2017/015780.
Written Opinion of the International Searching Authority dated Apr. 4, 2017 from corresponding to International Application No. PCT/US2017/015780.
International Search Report dated Apr. 10, 2017 from corresponding International Application No. PCT/US2017/014756.
Written Opinion of the International Searching Authority dated Apr. 10, 2017 from corresponding International Application No. PCT/US2017/014756.

\* cited by examiner

SENSING DEVICE, SENSING DEVICE SYSTEM, AND METHODS FOR MEASURING A CHARACTERISTIC OF A CONCRETE MIXTURE AND FOR PREDICTING A PERFORMANCE CHARACTERISTIC OF A CONCRETE MIXTURE

This application claims priority from U.S. Provisional Application No. 62/289,723 filed Feb. 1, 2016. This application claims the benefit of U.S. Provisional Application No. 62/343,635 filed May 31, 2016 and U.S. Provisional Application No. 62/356,378 filed Jun. 29, 2016. The contents of each of these applications are incorporated by reference.

TECHNICAL FIELD

This specification relates generally to the construction field, and more particularly to a sensing device, sensing device system, and methods for measuring a characteristic of a concrete mixture and for predicting a performance characteristic of a concrete mixture.

BACKGROUND

Concrete is generally used within the industry to refer to a mixture of cement, sand, stone, and water which upon aging turns into a hardened mass. The term concrete, as used in the specification and claims herein, means not only concrete as it is generally defined in the industry (cement, sand and stone), but it also means mortar (cement, sand and water) and cement (cement and water which hardens into a solid mass upon aging).

In the construction field, after a batch of concrete has been produced for use at a particular site, it is useful to be able to obtain data concerning certain performance characteristics such as the in-place strength of the batch. Accurate prediction of concrete performance can increase the quality of the end product, and can provide other benefits such as allowing the use of accelerated construction schedules.

Several methods for testing and monitoring in-place strength of a concrete mass have been incorporated into the American Standard Testing Methods, including ASTM C805 (The Rebound Number Method—the so-called Swiss Hammer Method), ASTM C597 (The Pulse Velocity (Sonic) Method), ASTM C74 (The Maturity Method), and ASTM C900 (The Pullout Strength Method).

In accordance with standards set forth in ASTM C31 (Standard Practice for Making and Curing Concrete Test Specimens in the Field), the compressive strength of concrete is measured to ensure that concrete delivered to a project meets the requirements of the job specification and for quality control. In order to test the compressive strength of concrete, cylindrical test specimens are cast in test cylinders and stored in the field until the concrete hardens.

In accordance with the standards, typically 4×8-inch or 6×12-inch test cylinders are used, and the concrete filed specimens are first stored within the project site location for their initial hardening, and then moved to a lab or a carefully selected location for a predetermined period of time and cured under moist conditions and a constant temperature of 20 dC. When making cylinders for acceptance of concrete, the field technician must test properties of the fresh concrete including temperature, slump, density (unit weight) and air content.

There is an ongoing need for improved systems and methods for measuring and predicting the strength and performance of concrete.

SUMMARY

In accordance with an embodiment, a sensing device is attached to the side of a concrete test cylinder. The sensing device has a concave side adapted to conform to a curvature of the outer side of the concrete test cylinder. The sensing device includes a temperature sensor and a humidity sensor. After concrete is poured into the test cylinder, the sensing device obtains temperature measurements and/or humidity measurements.

In one embodiment, the sensing device includes a housing and a cavity defined inside the housing. The temperature sensor and the humidity sensor are disposed within the cavity. The sensing device may also include a transmitter or other communication device disposed within the cavity.

In one embodiment, the sensing device includes a capillary needle disposed on and projecting outwardly from the concave side of the device. The capillary needle connects to a humidity sensor.

In accordance with another embodiment, a measurement system includes a concrete test cylinder. The side of the cylinder has an outer surface having a convex shape, and the side has particular thickness. A hole is disposed in the side of the cylinder. The measurement system also includes a sensing device. The sensing device has a concave side adapted to conform to the convex shape of the outer surface of the side of the concrete test cylinder. The sensing device includes a temperature sensor and a capillary needle which is disposed on the concave side of the sensing device and projects outwardly from the concave side. The capillary needle connects to a humidity sensor and has a length substantially equal to the thickness of the side of the cylinder.

In accordance with another embodiment, a method includes attaching a sensing device to a side of a concrete test cylinder, receiving temperature and humidity measurements from the sensing device, and computing maturity from temperature measurements which is used to generate predictions of strength of the concrete, with due regard to the humidity measurements.

In accordance with another embodiment, a communication system includes a network and a sensing device attached to a cylinder that contains a concrete mixture. The sensing device is adapted to obtain temperature measurements and humidity measurements. The sensing device is connected to the network. The communication system also includes a processor connected to the network, the processor being adapted to receive the temperature measurements and humidity measurements, and to generate a prediction of a performance characteristic of the concrete mixture based on the temperature and humidity measurements.

These and other advantages of the present disclosure will be apparent to those of ordinary skill in the art by reference to the following Detailed Description and the accompanying drawings.

DETAILED DESCRIPTION

Figure 1:
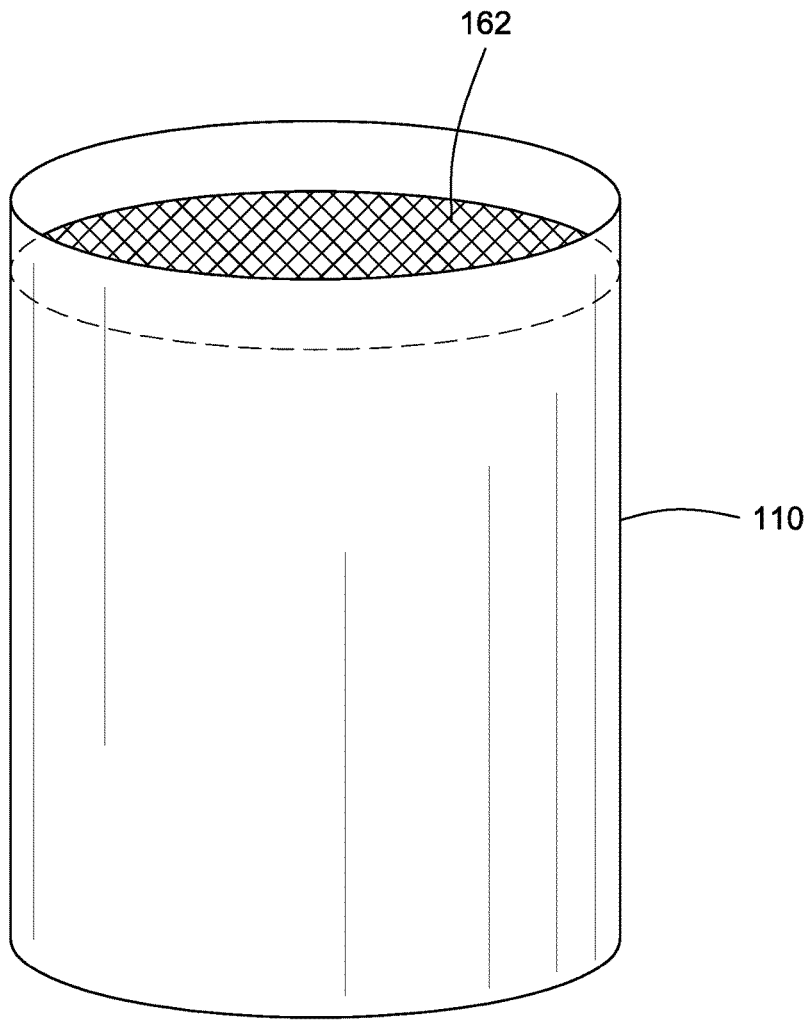
FIG. 1 shows an exemplary test cylinder containing a test specimen of concrete.

In accordance with standards set forth in ASTM C31 (Standard Practice for Making and Curing Concrete Test Specimens in the Field), the compressive strength of concrete is measured to ensure that concrete delivered to a project meets the requirements of the job specification and for quality control. In order to test the compressive strength of concrete, cylindrical test specimens are cast in test cylinders and stored in the field until the concrete hardens. FIG. 1 shows an exemplary test cylinder 110 containing a test specimen of concrete 162.

Figure 2A:
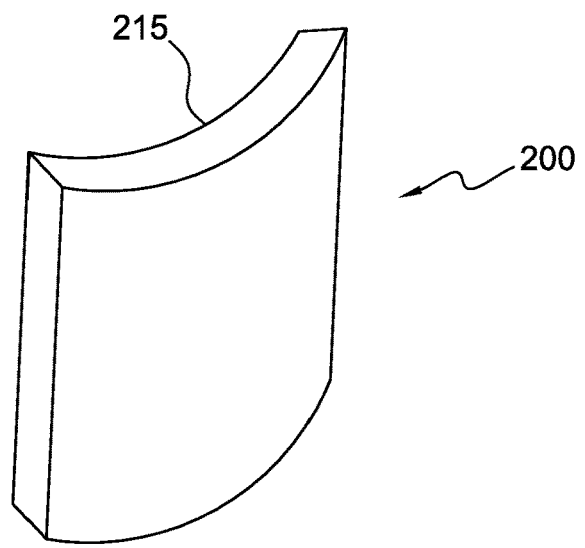
FIG. 2A shows a sensor patch in accordance with an embodiment.
Figure 2B:
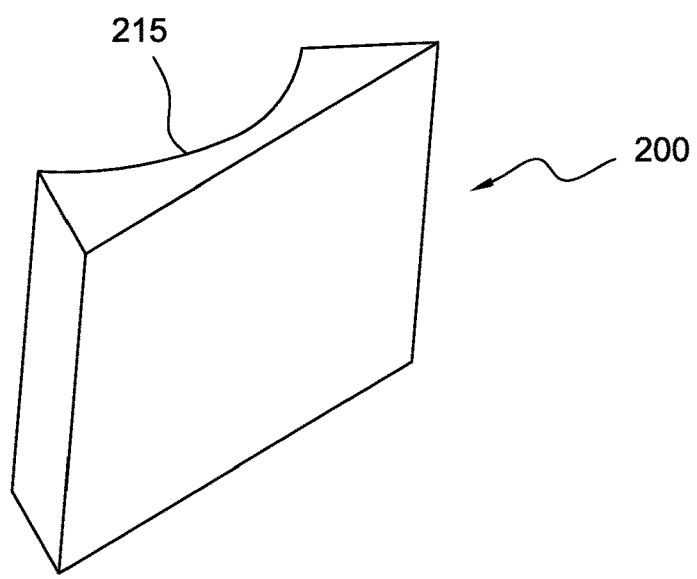
FIG. 2B shows a sensor patch in accordance with another embodiment.

FIG. 2A shows a sensor patch in accordance with an embodiment. Sensor patch 200 includes a sensing device. Sensor patch 200 may be any size and have any shape. In one embodiment, sensor patch 200 has a square shape and is approximately 30-50 mm on each side. In one embodiment, sensor patch 200 is approximately 3-15 mm thick. One side 215 of sensor patch 200 has a concave shape. In the illustrative embodiment of FIG. 2A, side 215 of sensor patch 200 has a concave shape; and the opposite side is convex. In another illustrative embodiment shown in FIG. 2B, side 215 of sensor patch 200 is concave; however, the opposite side is flat.

Sensor patch 200 is adapted to fit on the outer surface of a standard concrete test cylinder. Referring to the illustrative embodiment of FIG. 2A, for example, concave side 215 is shaped to conform to the curvature of the outer surface of a side of a concrete test cylinder. For example, sensor patch 200 may be adapted to fit on the outer surface of a side of a standard 4×8-inch or 6×12-inch concrete test cylinder. A sensor patch may be adapted to fit on other containers having other sizes, such as cubic 150 mm and 200 mm concrete molds used in Europe, in which case both sides of the sensor patch would be flat.

Figure 2C:
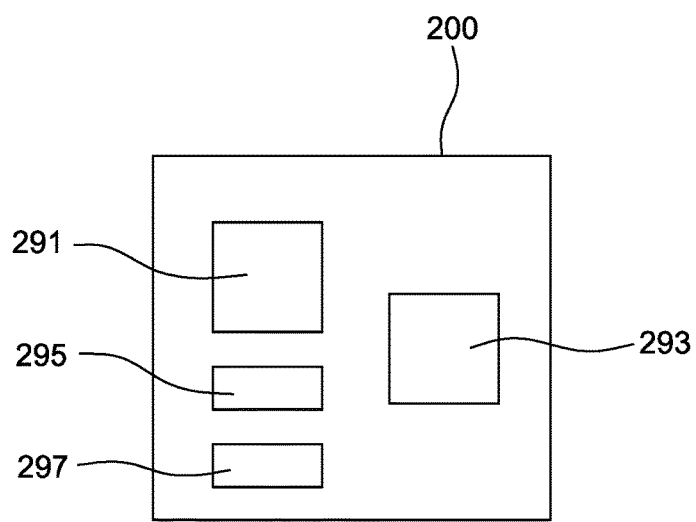
FIG. 2C shows components of a sensor patch in accordance with an embodiment.

FIG. 2C shows components of sensor patch 200 in accordance with an embodiment. Sensor patch 200 includes a temperature sensor 291 and a humidity sensor 293. Sensor patch 200 also includes GPS-based location detector. Sensor patch 200 also includes a communication device 297, which may be a transmitter or transceiver. Communication device 297 is capable of transmitting data (e.g., measurement data) to a remote device. For example, communication device 297 may transmit data wirelessly. Sensor patch 200 may include other types of sensors not shown in FIG. 2C.

It has been observed that heat flows readily through the side of a standard concrete test cylinder. As a result, temperature measurements obtained at or near the outer surface of a test cylinder can be used to determine, or to estimate, temperature and other characteristics of the concrete contained the test cylinder. Tests confirm that sensor patch temperature measurements are very close to concrete temperature inside the mold. Thus sensor patch devices can record sufficiently accurate temperatures without in any way intruding into the concrete inside the cylinder, and thus in any way making the test specimen unfit for a standard compression test. Thus, uniquely one can both record the test cylinder's temperature and perform an acceptable compression test on it.

Figure 3A:
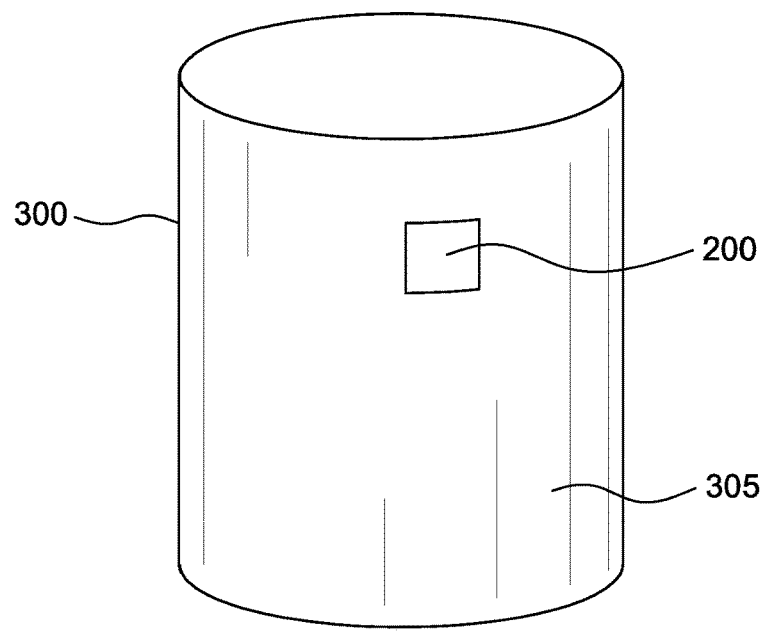
FIG. 3A shows a sensor patch attached to a concrete test cylinder in accordance with an embodiment.

Thus, in accordance with an embodiment, a sensor patch is attached to the side of a concrete test cylinder. A sensor patch may be attached, for example, by an adhesive, by a mechanical fastener, by a magnetic fastener, or by another mechanism. FIG. 3A shows sensor patch 200 attached to a test cylinder 300 in accordance with an embodiment. In particular, sensor patch 200 is attached to a side 305 of test cylinder 300. Because test cylinder 300 has a cylindrical shape, an outer surface of side 305 has a convex shape. When attached to side 305 of cylinder 300, concave edge 215 of sensor patch 200 allows the concave surface of sensor patch 200 to be flush with the convex outer surface of side 305 of cylinder 300.

Advantageously, the concave shape of sensor patch 200 allows a large portion of the surface of sensor patch 200 to be in contact with, or proximate to, the surface of side 305 of cylinder 300. This contact, or proximity, between a large portion of the surface of sensor patch 200 and the surface of the side of cylinder 300 enables sensor patch to obtain more accurate temperature measurements.

Figure 3B:
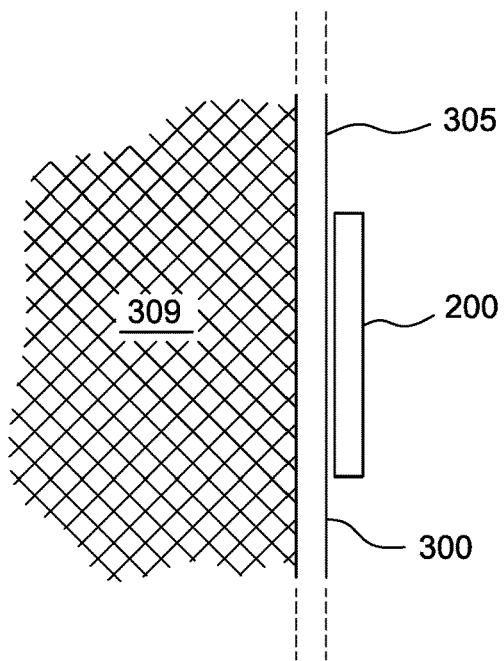
FIG. 3B shows a side-view cross-section of a sensor patch and of a concrete test cylinder in accordance with an embodiment.

FIG. 3B shows a side-view cross-section of test cylinder 300 and of sensor patch 200 in accordance with an embodiment. Concave side 215 of sensor patch 200 is in contact with side 305 of test cylinder 300. In the illustrative embodiment, test cylinder 300 holds a concrete mixture 309.

Figure 3C:
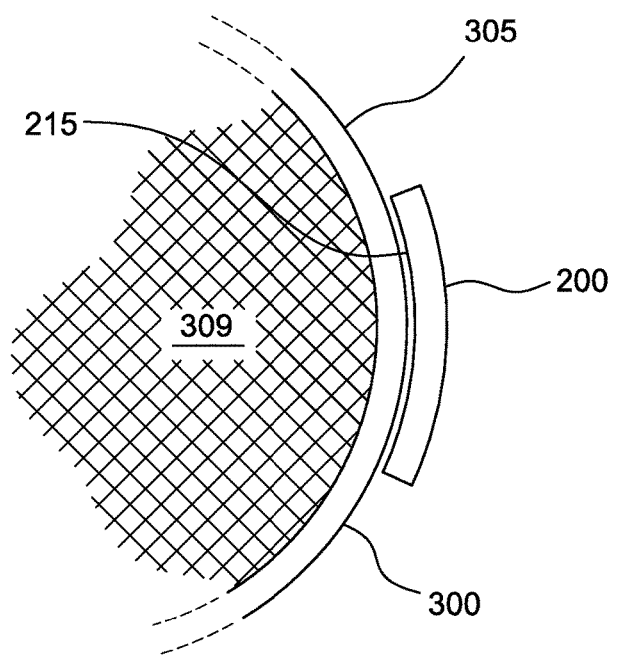
FIG. 3C shows a top-view cross-section of a sensor patch and of a concrete test cylinder in accordance with an embodiment.

FIG. 3C shows a top-view cross-section of test cylinder 300 and of sensor patch 200 in accordance with an embodiment. Concave side 215 of sensor patch 200 conforms to the convex shape of side 305 of cylinder 300.

In accordance with an embodiment, concrete is poured into cylinder 300. After the concrete is poured into cylinder 300, sensor patch 200 obtains temperature and humidity measurements. Sensor patch 200 may transmit the measurement data to a second device, such as a computer located at a remote location.

Figure 4A:
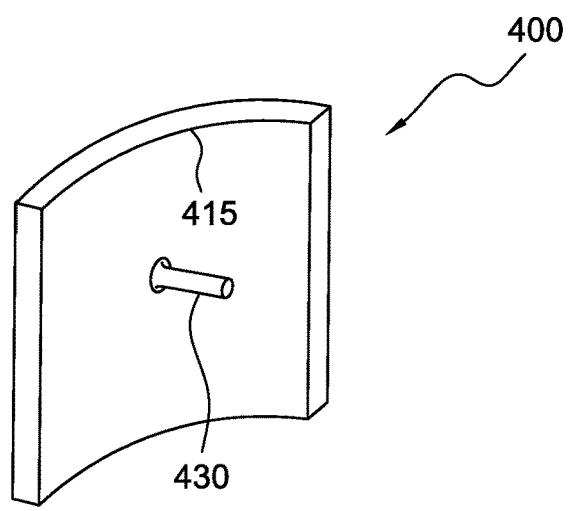
FIG. 4A shows a perspective view of a sensor patch in accordance with an embodiment.
Figure 4B:
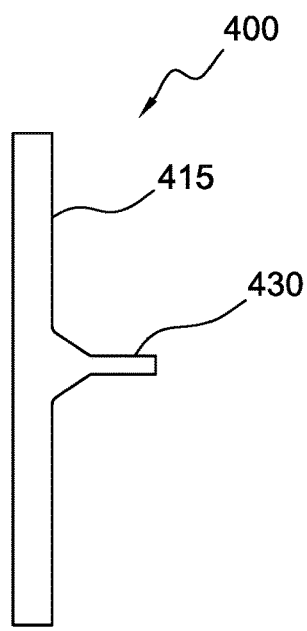
FIG. 4B shows a cross-section of sensor patch in accordance with an embodiment.

FIGS. 4A-4B show a sensor patch in accordance with another embodiment. FIG. 4A shows a perspective view of a sensor patch 400 in accordance with an embodiment. FIG. 4B shows a cross-section of sensor patch 400 in accordance with an embodiment. Sensor patch 400 includes a concave side 415, and a capillary needle 430 which is disposed on concave side 415 and projects outwardly from concave side 415. While the sensor patch 400 is reusable, the capillary needle is disposable since after each test it can be removed and another needle reinstated into the sensor. To protect the sensor from water intrusion, the sensor end of the capillary needle is sealed in Gortex which allows passage of water vapor, but not water liquid.

Capillary needle 430 connects to a humidity sensor. For example, capillary needle 430 may be connected to humidity sensor 293. Capillary needle 430 has a length approximately equal to the thickness of the side of a concrete test cylinder. In one embodiment, the side of a standard concrete test cylinder is approximately 2-3 mm thick. Therefore, capillary needle 430 has a length of approximately 2-3 mm.

In accordance with an embodiment, the side of a test cylinder has a small hole, which may be, for example 1-3 mm in diameter. In accordance with an embodiment, sensor patch 400 is attached to the side of the test cylinder in a manner that causes capillary needle 430 to penetrate the hole in the side of the cylinder.

Figure 5A:
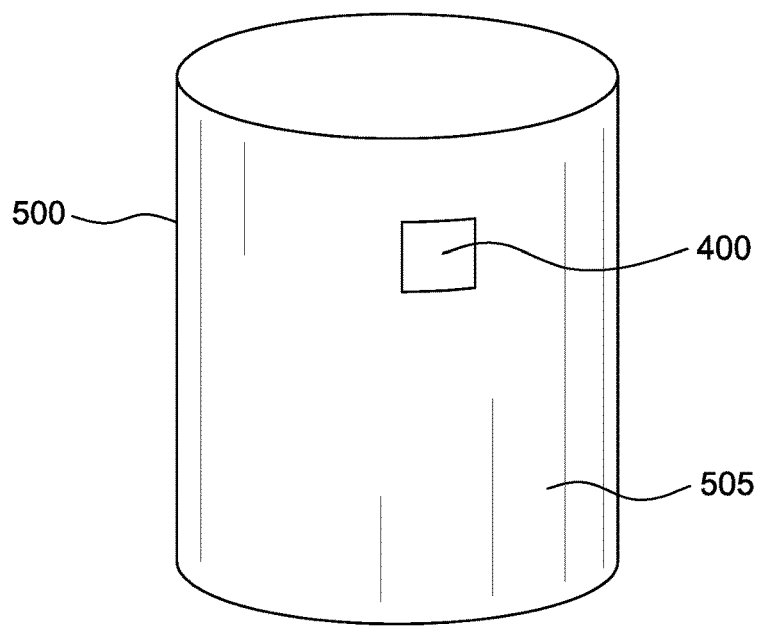
FIG. 5A shows sensor patch attached to a side of a concrete test cylinder in accordance with an embodiment.
Figure 5B:
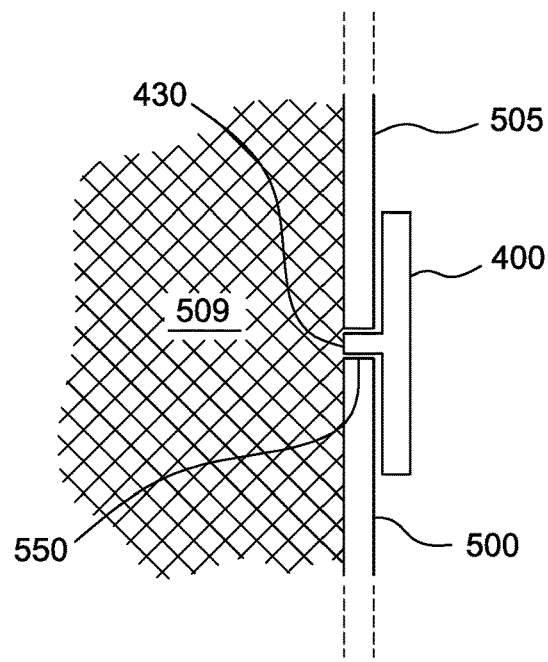
FIG. 5B shows a cross-section of a sensor patch and of a side of a concrete test cylinder in accordance with an embodiment.

FIG. 5A shows sensor patch 400 attached to a side 505 of a test cylinder 500 in accordance with an embodiment. FIG. 5B shows a cross-section of sensor patch 400 and of side 505 of test cylinder 500 in accordance with an embodiment. In the illustrative embodiment, test cylinder 500 holds a concrete mixture 509.

A hole 550 is present in side 505 of test cylinder 505. Sensor patch 400 is attached such that sensor patch 400 is proximate to side 505 of test cylinder 400, and capillary needle 430 penetrates into hole 550. Because capillary needle 430 has a length that corresponds to the thickness of side 505 of cylinder 500, capillary needle 430 penetrates into hole 550 and extends through the length of hole 550, but does not project out of hole 550 on the opposite side (i.e., capillary needle 430 does not extend into the inside of cylinder 500). Consequently, capillary needle 430 does not penetrate into concrete mixture 509 within test cylinder 500.

After sensor patch 400 is attached to cylinder 500, temperature sensor 291 (shown in FIG. 2C) of sensor patch 400 obtains temperature measurements. Capillary needle 430 obtains humidity measurements. Sensor patch 400 may transmit temperature and humidity measurement data to a second device.

Figure 6A:
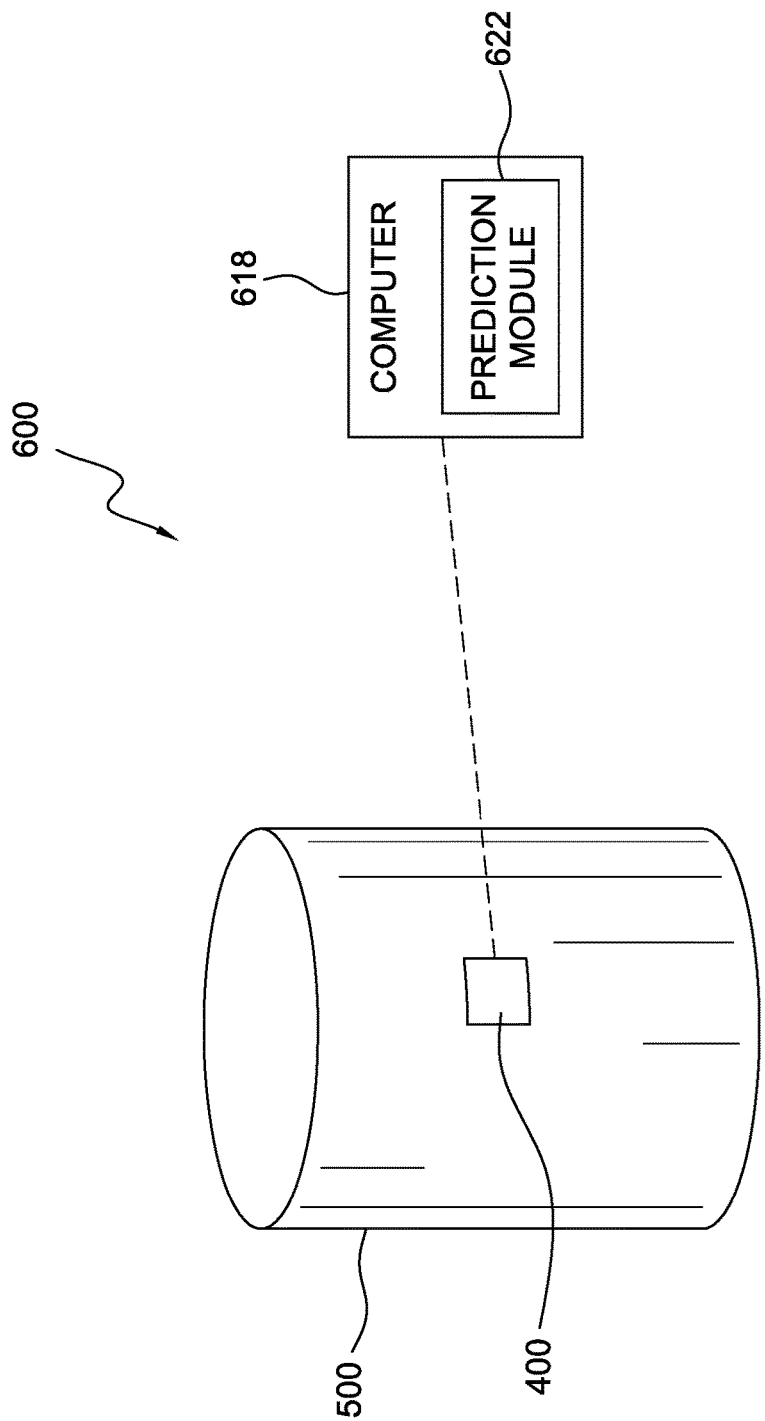
FIG. 6A shows a communication system in accordance with an embodiment.

In accordance with an embodiment, temperature and humidity measurements obtained by a sensor patch are used to determine a prediction of a characteristic of the concrete mixture contained in a test cylinder. FIG. 6A shows a communication system in accordance with an embodiment. Communication system 600 includes test cylinder 500, sensor patch 400, and a computer 618. Computer 618 includes a prediction module 622, which is adapted to generate a prediction of a selected characteristic of a concrete mixture based on temperature and humidity measurements. Methods for determining strength from maturity are known, and maturity itself can be computed for a measured curing temperature versus age profile, and other characteristics of a concrete mixture based on temperature and humidity measurements are also known.

Figure 6B:
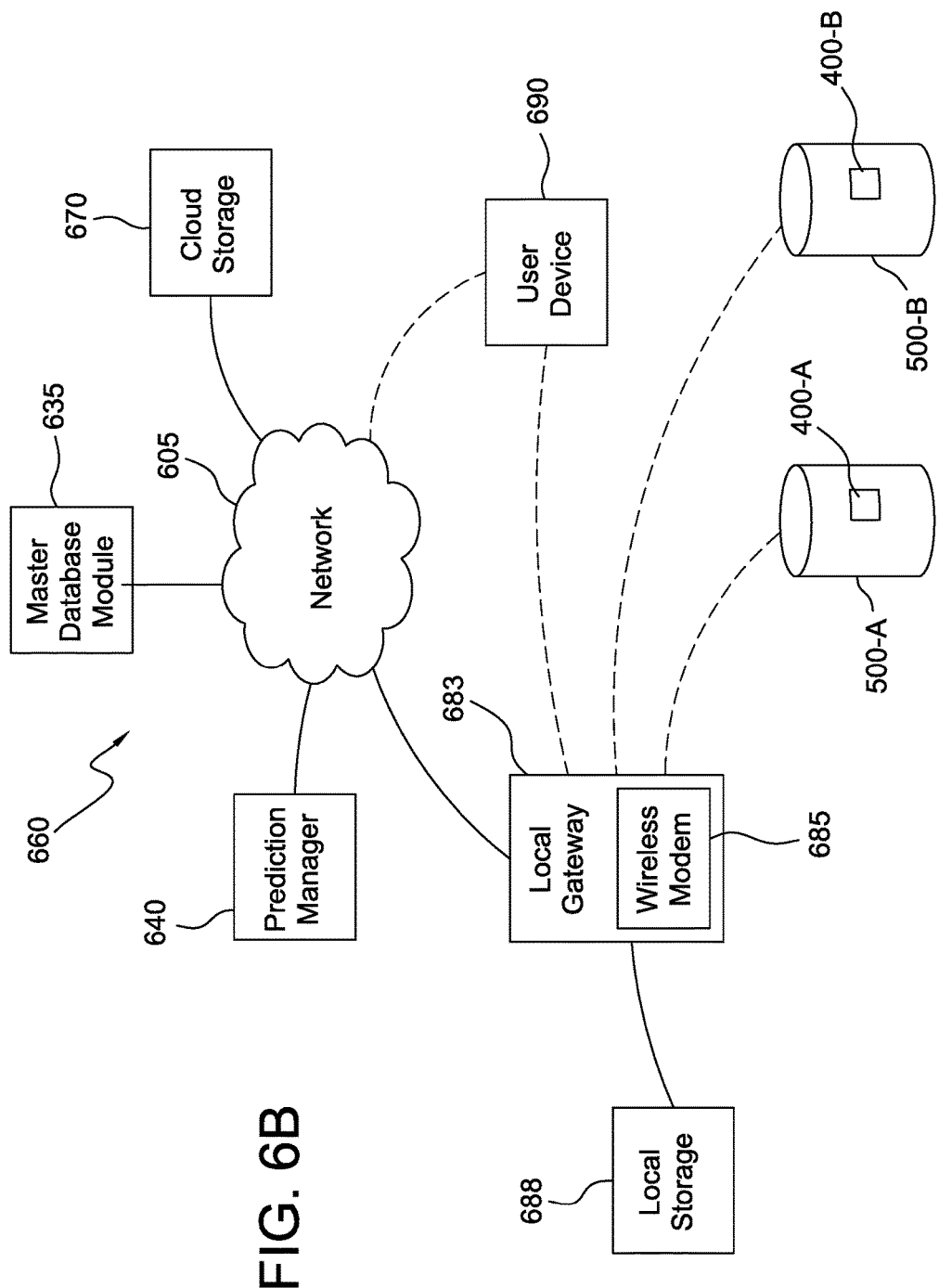
FIG. 6B shows a communication system in accordance with another embodiment.

FIG. 6B shows a communication system in accordance with another embodiment. Communication system 660 includes a network 605, which may include the Internet, for example, a master database module 635, a prediction manager 640, and a cloud storage 670.

Communication system 660 also includes a local gateway 683, which is connected to network 605. Local gateway 683 includes a wireless modem 685. Local gateway 683 is linked to a plurality of sensor patch systems 400-A, 400-B, which are attached to respective test cylinders 500-A, 500-B. Local gateway 683 is also linked to a local storage 688. Local gateway 683 may from time to time store data, such as measurement data received from sensor patch systems 400, in local storage 688. Local gateway 683 and local storage 688 may be located at or near a construction site, for example.

Sensor patch systems 400-A, 400-B are disposed on respective test cylinders 500-A, 500-B, which hold respective specimens of concrete. Using methods and apparatus similar to those described above, each sensor patch system 400 obtains measurements related to a respective specimen of concrete. Each sensor patch system 400 transmits measurement data to master database module 635 via local gateway 683 and network 605. For example, each sensor patch system 400 may transmit measurement data wirelessly to local gateway 683, which transmits the measurement data to master database module 635 via network 605. Each sensor patch system 400 may also transmit an identifier uniquely identifying itself. For example, an RFID tag embedded in each sensor patch 400 may transmit identification information. Communication system 660 may include any number of sensor patch systems attached to respective test cylinders.

In one embodiment, multiple sensor patch systems 400 may be located at a single location (e.g., a single construction site). In another embodiment, multiple sensor patch systems 400 may be located at multiple locations (e.g., at multiple construction sites across large geographical areas such as States and countries).

Communication system 660 also includes a user device 690, which may be a personal computer, laptop device, tablet device, cell phone, or other processing device which is located at a construction site and used by a technician at the site. User device 690 may communicate with network 605, with local gateway 683, and/or with other devices within communication system 660.

Master database module 635 receives measurement data from one or more sensor patch systems 400 and may analyze the measurement data. In the illustrative embodiment, master database module 635 transmits the measurement data to prediction manager 640 (or otherwise makes the data available to prediction manager 640). Prediction manager 640 may generate predictions concerning the behavior of one or more concrete specimens. For example, prediction manager 640 may receive temperature, humidity, and/or location data from sensor patch system 400-A and, based on the measurement data, generate predictions regarding the water-to-cementitious ratio, durability, strength, slump, maturity, etc., of the concrete specimen in cylinder 500-A. Similarly, for example, prediction manager 640 may receive temperature, humidity, and/or location data from sensor patch system 400-B and, based on the measurement data, generate prediction data regarding the water-to-cementitious ratio, durability, strength, slump, maturity, etc., of the concrete specimen in cylinder 500-B. In one embodiment, the measurement data received by master database module 635 is provided to a real-time model to project setting behavior and strength for the entire batch of concrete. In another embodiment, the measurement data is continually subject to statistical analysis to generate real-time projections, control charts, etc. Master database module 635 may store the prediction data in cloud storage 670. For example, prediction data may be stored in a database. Other data structures may be used to store prediction data.

In an embodiment, all measured data are stored and consolidated in a cloud database, and then the prediction manager 640 accesses the data, and by using scientific, technological, statistical, data mining, or neural network algorithms, provides the needed strength, maturity, form scheduling, and alarming projections and actions.

In one embodiment, master database module 635 may transmit measurement data and/or prediction information relating to water-to-cementitious ratio, durability, strength, slump, maturity, etc. to a user device such as user device 690 to enable a technician to access and view the information. For example, user device 690 may display measurement data and/or prediction data on a web page, or in another format.

In one embodiment, cloud storage 670 may comprise a cloud storage system. Data obtained by sensor patch system 400 may be transmitted to and saved in cloud storage 670 in real-time. A cloud implementation such as that illustrated by FIG. 6B may allow data from projects in multiple regions or multiple countries to be auto-consolidated in a single database.

Suppose, then, that concrete is poured into cylinders 500-A and 500-B. Sensor patch systems 400-A and 400-B may obtain temperature and humidity measurements, and the data may be used to generate predictions for certain performance characteristics of the concrete in the cylinders.

Figure 7:
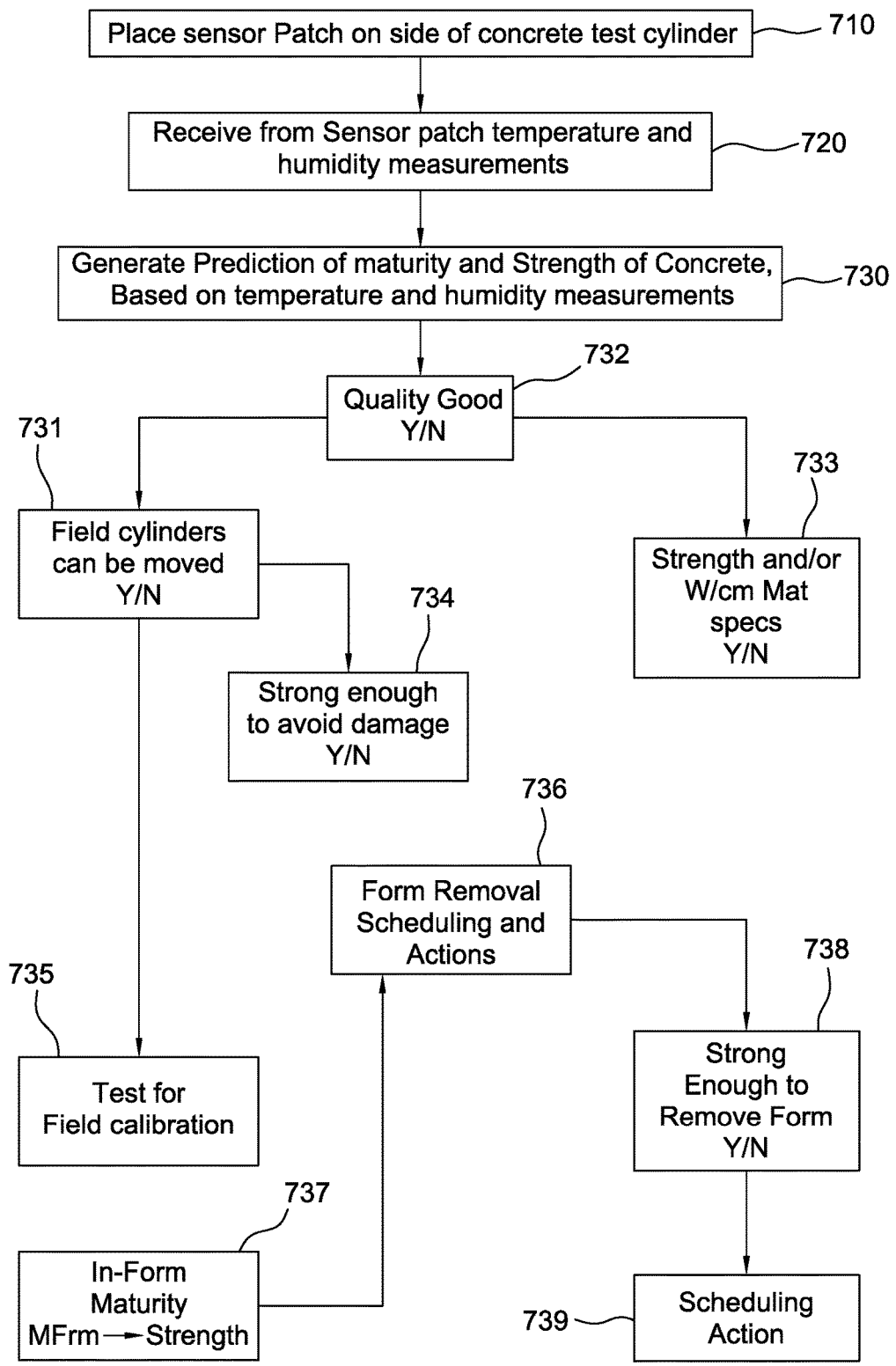
FIG. 7 is a flowchart of a method in accordance with an embodiment.

FIG. 7 is a flowchart of a method in accordance with an embodiment. At step 710, a sensor patch is attached to the side of a concrete test cylinder. For example, in the illustrative embodiment of FIG. 6B, sensor patch 400-A is attached to test cylinder 500-A. After sensor patch 400-A is attached, the sensor patch obtains temperature and humidity measurements.

At step 720, temperature and humidity measurements are received from the sensor patch. Sensor patch 400-A transmits the measurements to master database module 635. Master database module 635 receives the temperature and humidity measurements and transmits the data to prediction manager 640.

At step 730, predictions of maturity and strength of the concrete are generated based on the temperature and humidity measurements. Thus, prediction manager 640 generates predictions of maturity and strength for the concrete in test cylinder 500-A, based on the temperature and humidity measurements obtained by sensor patch 400-A.

Maturity is obtained by measuring concrete temperature versus time by applying ASTM C74 formulae. No matter what the field temperature profile, M expresses the curing age of concrete as an equivalent at a standard curing temperature such as 20 dC.

For each concrete class of given mix design, under lab or field conditions, a Strength versus M curve is established.

Accordingly, if the field clock time age (time since concrete was poured + transportation time) is for instance 50 hrs, one can convert to an M age of, for example, 32 hrs, and look up the strength.

Blocks 731 and 734 relate to treatment of field cylinders. To measure quality, field test cylinders are taken at concrete discharge or pour locations (for instance at pump discharge, on the $10^{th}$ floor). The field tests must not be moved until concrete is strong enough to avoid damage, per ASTM and many other specifications. If moved prematurely, the tests will break low (since the cylinder could have crack during transportation), and are invalid, or disputes could occur between the testing lab, contractor, owner, and concrete vendor.

Blocks 732 and 733 relate to quality determination. Quality is usually evaluated by determining cylinder compressive strength at 28 M days, also sometimes at 7 M days or even 1 to 2 M days. The discussed approach will allow quality determination at any age by reference to current field and historical data on the basis of strength. If a closed loop process is being used, then mixture proportions for the test cylinders would be known, and converted to W/Cm ratio and strength by reference to calibration data.

Blocks 735-739 relate to form removal scheduling and actions. Measurements obtained from a sensor patch that are transmitted to a remote database, can provide concrete quality data-driven scheduling for form removal, and thereby allow for more efficient construction scheduling. A filed cylinder is used to develop Strength—M field calibration. In one embodiment, a sensor patch disposed on formwork will measure M-form, and thereby determine if concrete strength is such that the formwork could be stripped. If the answer to form stripping is negative, then the scheduling will be adjusted, but also action will be taken so as to maintain construction speed. Actions could include switching to stronger, faster setting concrete, using insulated formwork, erecting wind barriers, adding accelerating chemicals, etc. The data obtained by a sensor patch could also result in the reverse situation, namely that concrete sets too fast, and its setting and strength gain rate may need to be slowed down so as to make it constructible.

Advantageously, apparatus, systems, and methods described herein will increase concrete testing and quality management efficiency, and improve quality through automated real time data, that are auto-saved to remote databases and allow for full transparency. Apparatus, systems, and methods described herein make possible a more efficient construction process and construction rate by enabling a data-driven form removal scheduling approach. Self-evidently, when planning and scheduling concrete construction, the scheduling can best occur if concrete strength at early and later ages are known. This is particularly important during the construction process itself. Apparatus, systems, and methods described herein create the needed data automatically to schedule and make form stripping decisions on the basis of measurements, and not just past experience and guesswork.

Figure 8:
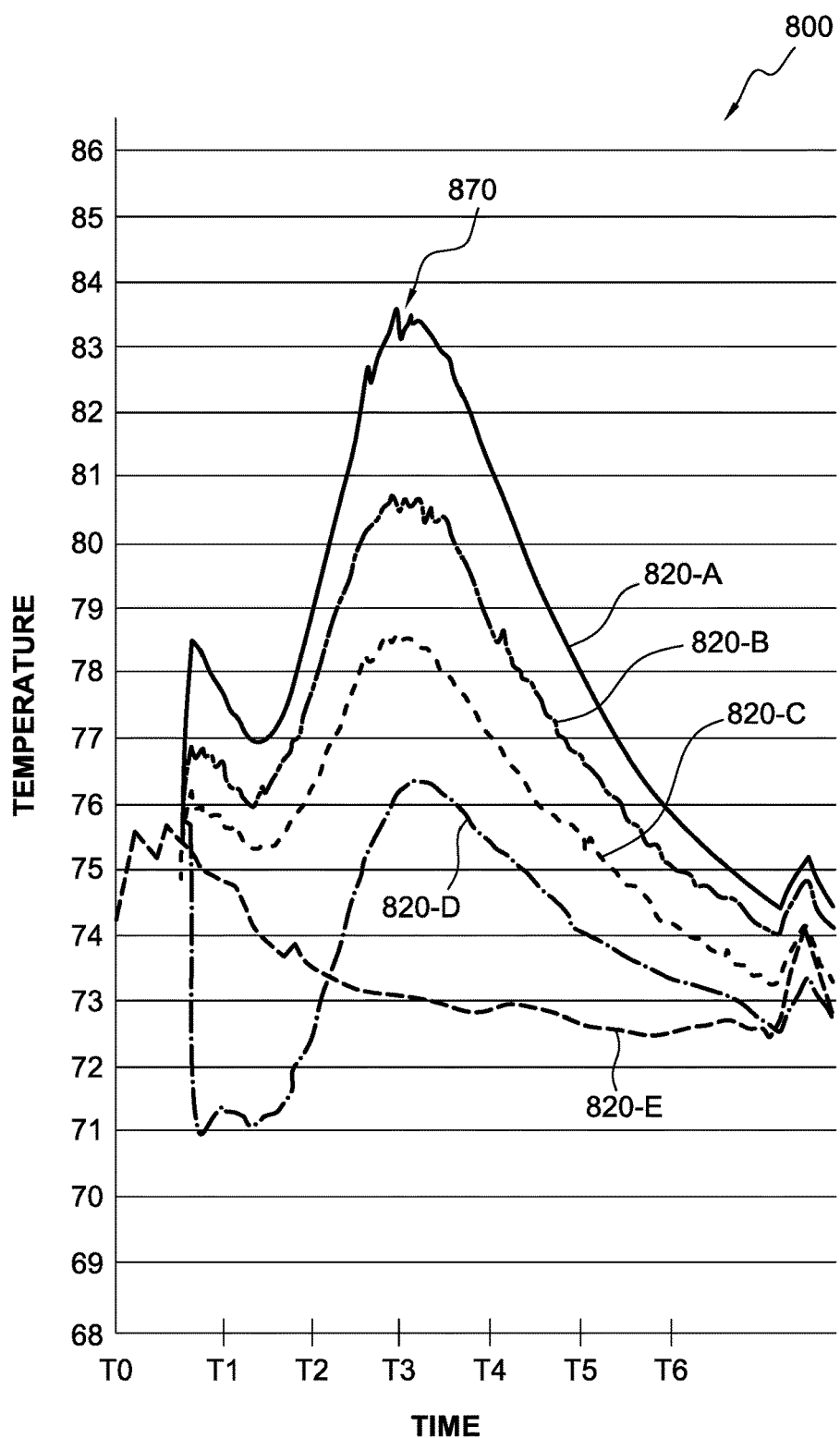
FIG. 8 includes a graph showing observed temperature over time measured after a concrete mixture has been poured into a test cylinder.

FIG. 8 includes a graph showing observed temperature over time measured after a concrete mixture has been poured into a test cylinder. Graph 800 includes five sets of temperature measurements 820-A, 820-B, 820-C, 820-D, and 820-E, each reflecting temperature of concrete in a test cylinder. The observed measurements show that after the concrete mixture is poured into the test cylinder, temperature begins at an initial temperature, rises from an initial temperature to a maximum (such as point 870), and then gradually decreases. In other examples, a specimen of a concrete mixture may demonstrate a different temperature profile. Advantageously, knowledge of the temperature profile associated with a particular specimen of concrete can be used to improve predictions of other characteristics of the concrete, such as strength, maturity, etc.

In various embodiments, the method steps described herein, including the method steps described in FIG. 7, may be performed in an order different from the particular order described or shown. In other embodiments, other steps may be provided, or steps may be eliminated, from the described methods.

Systems, apparatus, and methods described herein may be implemented using digital circuitry, or using one or more computers using well-known computer processors, memory units, storage devices, computer software, and other components. Typically, a computer includes a processor for executing instructions and one or more memories for storing instructions and data. A computer may also include, or be coupled to, one or more mass storage devices, such as one or more magnetic disks, internal hard disks and removable disks, magneto-optical disks, optical disks, etc.

Systems, apparatus, and methods described herein may be implemented using computers operating in a client-server relationship. Typically, in such a system, the client computers are located remotely from the server computer and interact via a network. The client-server relationship may be defined and controlled by computer programs running on the respective client and server computers.

Systems, apparatus, and methods described herein may be used within a network-based cloud computing system. In such a network-based cloud computing system, a server or another processor that is connected to a network communicates with one or more client computers via a network. A client computer may communicate with the server via a network browser application residing and operating on the client computer, for example. A client computer may store data on the server and access the data via the network. A client computer may transmit requests for data, or requests for online services, to the server via the network. The server may perform requested services and provide data to the client computer(s). The server may also transmit data adapted to cause a client computer to perform a specified function, e.g., to perform a calculation, to display specified data on a screen, etc.

Systems, apparatus, and methods described herein may be implemented using a computer program product tangibly embodied in an information carrier, e.g., in a non-transitory machine-readable storage device, for execution by a programmable processor; and the method steps described herein, including one or more of the steps of FIG. 7, may be implemented using one or more computer programs that are executable by such a processor. A computer program is a set of computer program instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Figure 9:
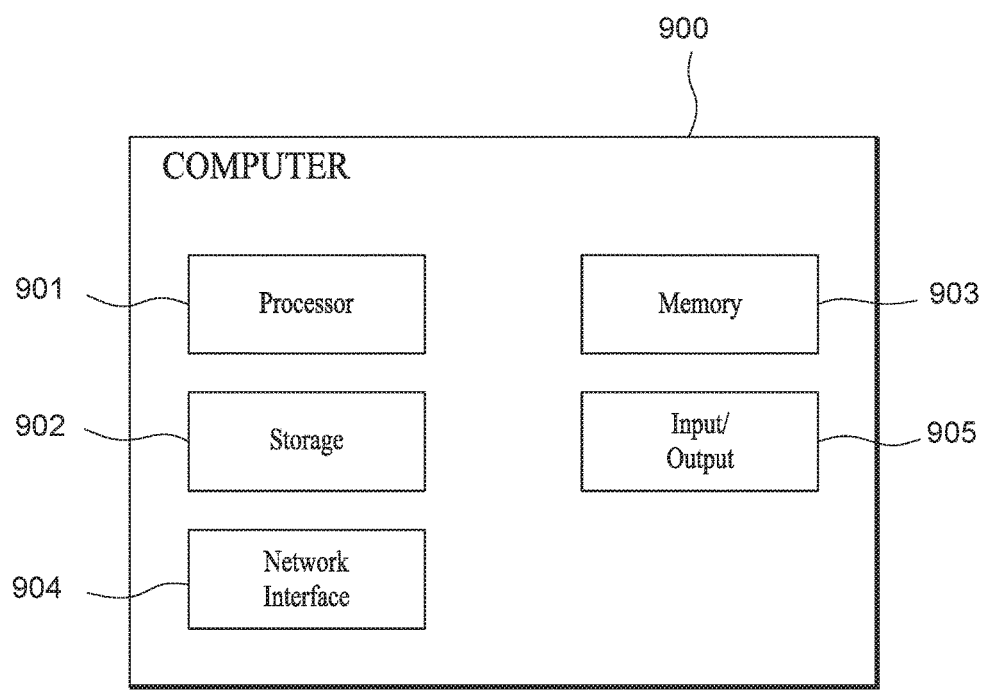
FIG. 9 shows an exemplary computer which may be used to implement certain embodiments.

A high-level block diagram of an exemplary computer that may be used to implement systems, apparatus and methods described herein is illustrated in FIG. 9. Computer 900 includes a processor 901 operatively coupled to a data storage device 902 and a memory 903. Processor 901 controls the overall operation of computer 900 by executing computer program instructions that define such operations. The computer program instructions may be stored in data storage device 902, or other computer readable medium, and loaded into memory 903 when execution of the computer program instructions is desired. Thus, the method steps of FIG. 7 can be defined by the computer program instructions stored in memory 903 and/or data storage device 902 and controlled by the processor 901 executing the computer program instructions. For example, the computer program instructions can be implemented as computer executable code programmed by one skilled in the art to perform an algorithm defined by the method steps of FIG. 7. Accordingly, by executing the computer program instructions, the processor 901 executes an algorithm defined by the method steps of FIG. 7. Computer 900 also includes one or more network interfaces 904 for communicating with other devices via a network. Computer 900 also includes one or more input/output devices 905 that enable user interaction with computer 900 (e.g., display, keyboard, mouse, speakers, buttons, etc.).

Processor 901 may include both general and special purpose microprocessors, and may be the sole processor or one of multiple processors of computer 900. Processor 901 may include one or more central processing units (CPUs), for example. Processor 901, data storage device 902, and/or memory 903 may include, be supplemented by, or incorporated in, one or more application-specific integrated circuits (ASICs) and/or one or more field programmable gate arrays (FPGAs).

Data storage device 902 and memory 903 each include a tangible non-transitory computer readable storage medium. Data storage device 902, and memory 903, may each include high-speed random access memory, such as dynamic random access memory (DRAM), static random access memory (SRAM), double data rate synchronous dynamic random access memory (DDR RAM), or other random access solid state memory devices, and may include non-volatile memory, such as one or more magnetic disk storage devices such as internal hard disks and removable disks, magneto-optical disk storage devices, optical disk storage devices, flash memory devices, semiconductor memory devices, such as erasable programmable read-only memory (EPROM), electrically erasable programmable read-only memory (EEPROM), compact disc read-only memory (CD-ROM), digital versatile disc read-only memory (DVD-ROM) disks, or other non-volatile solid state storage devices.

Input/output devices 905 may include peripherals, such as a printer, scanner, display screen, etc. For example, input/output devices 905 may include a display device such as a cathode ray tube (CRT) or liquid crystal display (LCD) monitor for displaying information to the user, a keyboard, and a pointing device such as a mouse or a trackball by which the user can provide input to computer 900.

Any or all of the systems and apparatus discussed herein, including sensor patch 200, sensor patch 400, communication device 297, computer 618, master database module 635, prediction manager 640, cloud storage 670, local gateway 683, local storage 688, and user device 690, and components thereof, may be implemented using a computer such as computer 900.

One skilled in the art will recognize that an implementation of an actual computer or computer system may have other structures and may contain other components as well, and that FIG. 9 is a high level representation of some of the components of such a computer for illustrative purposes.

In other embodiments, other methods and apparatus may be used to place a temperature sensor, a humidity sensor, and/or other sensors in contact with or in proximity to a concrete test cylinder in order to obtain temperature measurements, humidity measurements, etc. for the purpose of predicting a performance characteristic of a specimen of concrete inside the cylinder.

Figure 10A:
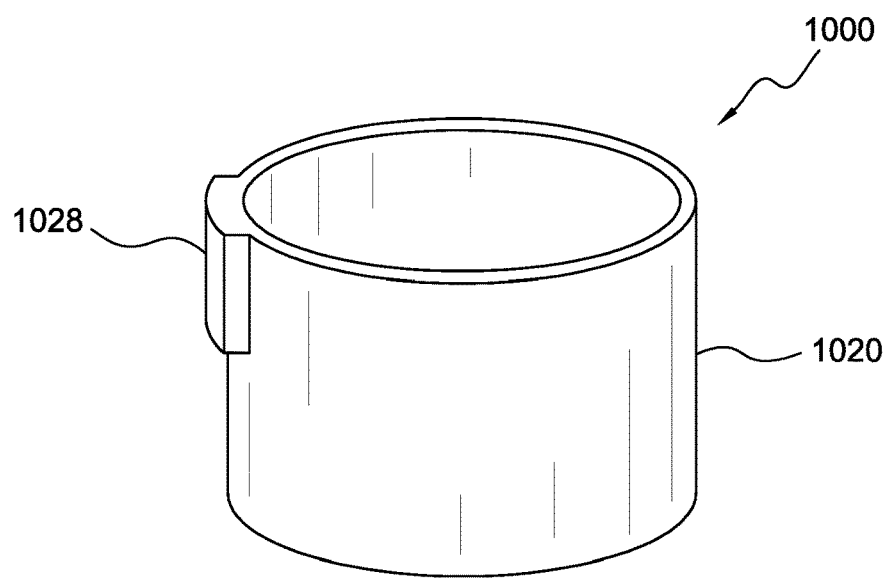
FIG. 10A shows a sensing system in accordance with an embodiment.

For example, FIG. 10A shows a sensing system 1000 in accordance with another embodiment. Sensing system 1000 includes a cylindrical container 1020 with an open top, and a pocket 1028. Pocket 1028 is disposed on a wall of container 1000.

Figure 10B:
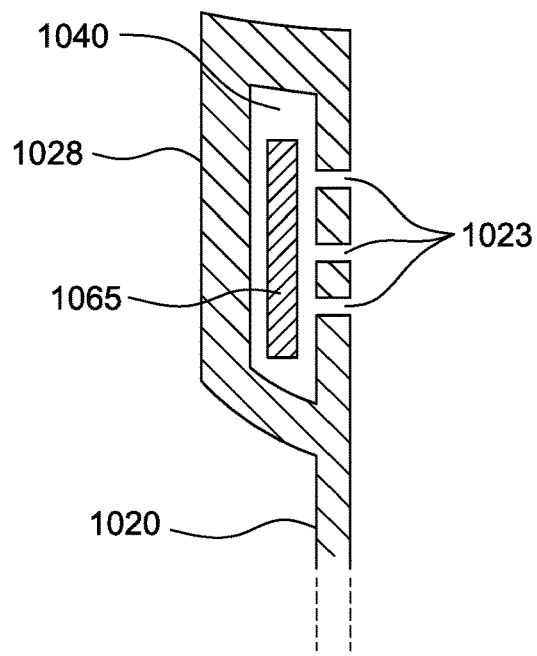
FIG. 10B shows a cross-section of container and of a pocket in accordance with an embodiment.

FIG. 10B shows a cross-section of container 1020 (of sensing system 1000) and of pocket 1028 in accordance with an embodiment. Pocket 1028 is constructed as an integral part of container 1020. Pocket 1028 includes an enclosed volume 1040. A plurality of holes 1023 are located in the interior portion of wall 1020, and connect volume 1040 with the interior space of container 1020.

A temperature sensor 1065 is disposed within volume 1040. Advantageously, holes 1023 allow an exchange of heat between container 1020 and volume 1028, enabling temperature sensor 1065 to obtain temperature measurements associated with a specimen of concrete contained in container 1020.

Figure 10C:
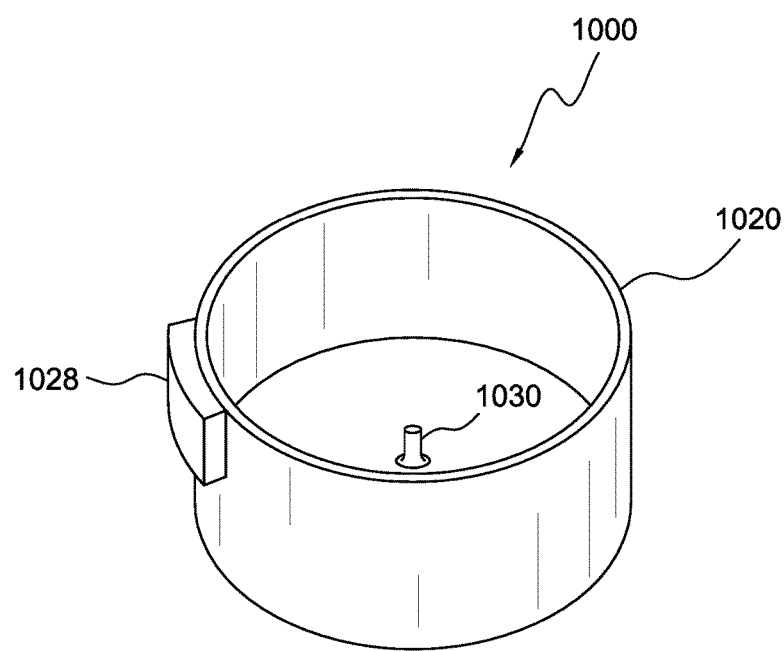
FIG. 10C shows a top view of a sensing system in accordance with an embodiment.

FIG. 10C shows a top view of sensing system 1000 in accordance with an embodiment. A capillary needle 1030 is disposed on the bottom surface of container 1020. Capillary needle 1030 projects upward from the bottom surface of container 1020. Capillary needle connects to a humidity sensor.

Figure 11A:
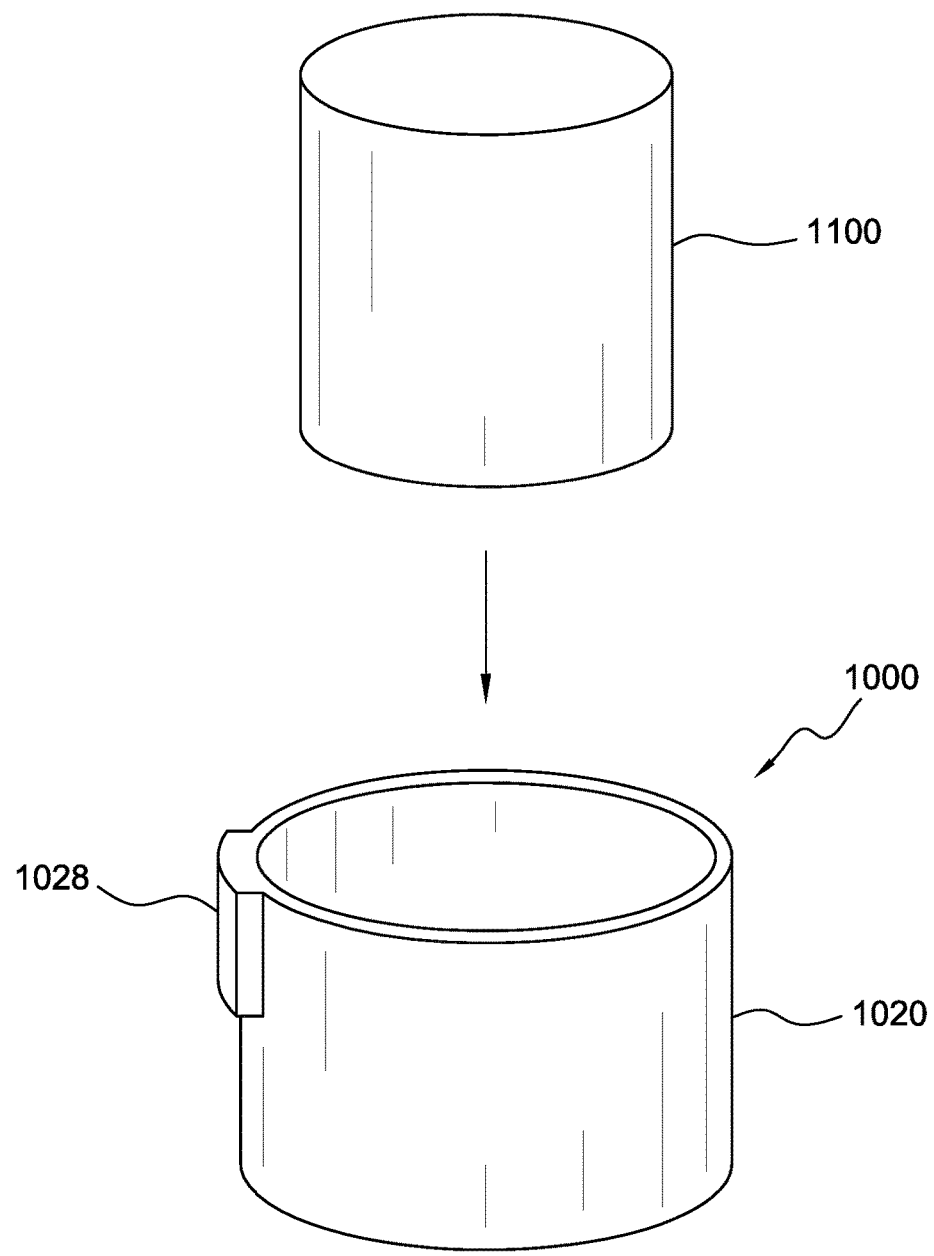
FIG. 11A shows a sensing system and a concrete test cylinder in accordance with an embodiment.
Figure 11B:
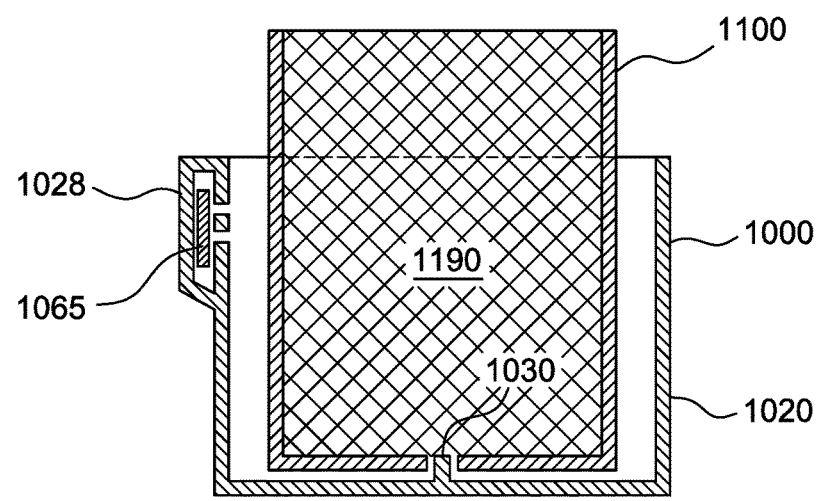
FIG. 11B shows a concrete test cylinder placed in sensing system in accordance with an embodiment.

In accordance with an embodiment illustrated in FIG. 11A, container 1020 is adapted to receive a concrete test cylinder 1100. FIG. 11B shows concrete test cylinder 1100 placed in sensing system 1000. When test cylinder 1100 is lowered into cylinder 1020, capillary needle 1030 penetrates through the bottom surface of test cylinder 1100. In one embodiment, a user pushes down on test cylinder 1100 to cause capillary needle 1030 to penetrate through the material of the test cylinder, effectively creating a hole in the material. In another embodiment, as concrete is poured into test cylinder 1100, the weight of the concrete causes test cylinder 1100 to push down on capillary needle, causing capillary needle 1030 to penetrate through the material of the test cylinder, effectively creating a hole in the material. As shown in FIG. 11B, capillary needle 1030 penetrates through the material of the bottom surface of test cylinder. In one embodiment, capillary needle 1030 may include a material (such as Gortex, for example) which prevents the concrete mixture from coming into contact with capillary needle 1030 but allows the passage of moisture to enable capillary needle to obtain humidity measurements.

After concrete is poured into concrete test cylinder 1100 and concrete test cylinder 1100 is placed into sensing system 1000, temperature sensor 1065 begins to obtain temperature measurements, and capillary needle 1030 begins to obtain humidity measurements. In a manner similar to those discussed above, temperature and humidity measurements may be transmitted to a remote device and used to generate a prediction of a performance characteristic for the concrete 1190 in test cylinder 1100.

Figure 12A:
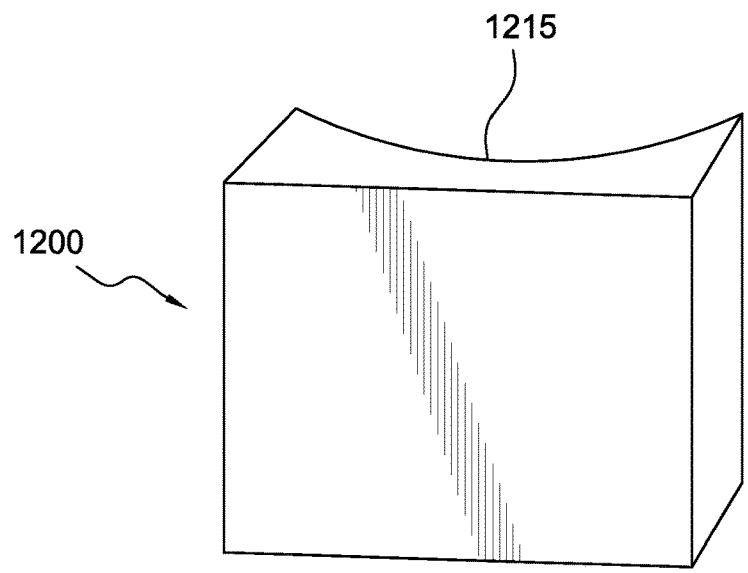
FIG. 12A shows a first side of a sensor patch in accordance with an embodiment.
Figure 12B:
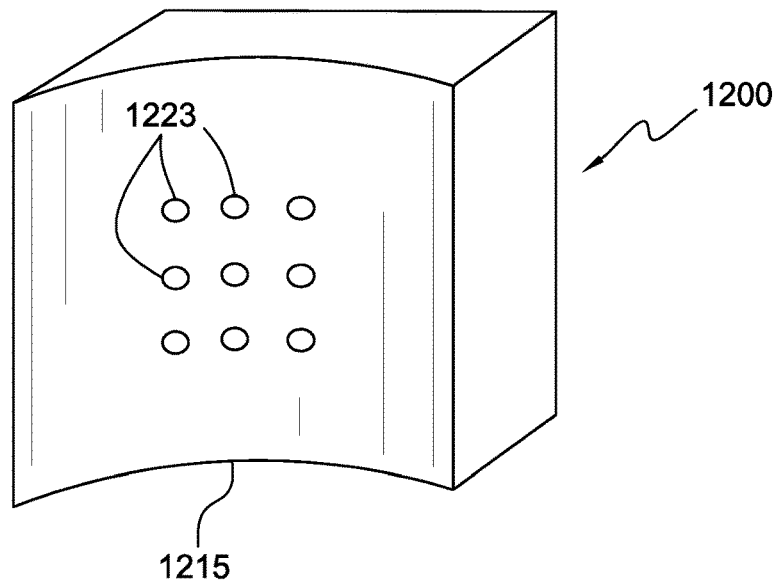
FIG. 12B shows a second (opposite) side of the sensor patch of FIG. 12A.
Figure 12C:
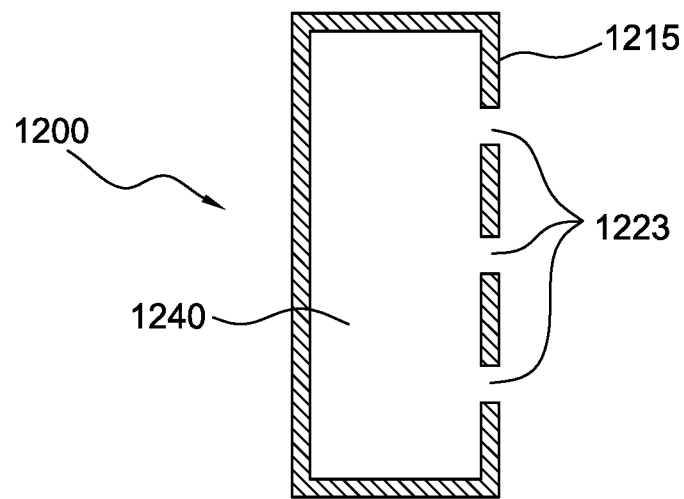
FIG. 12C shows a side-view cross-section of the sensor patch of FIG. 12A.
Figure 12D:
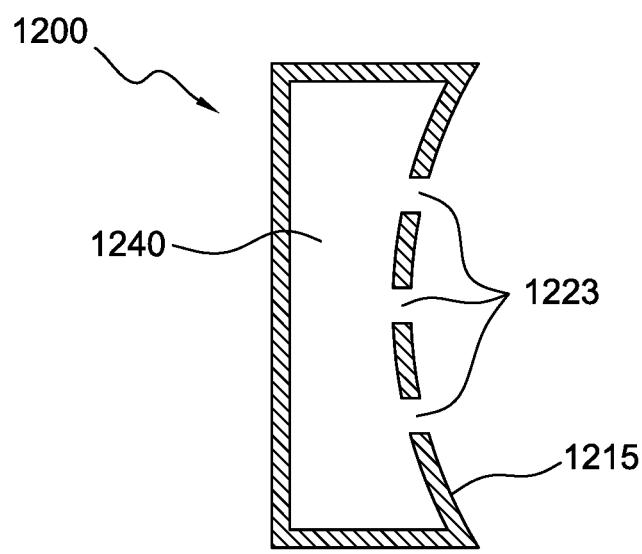
FIG. 12D shows a top-view cross-section of the sensor pouch of FIG. 12A.

FIGS. 12A-12D show a sensor patch in accordance with an embodiment. FIG. 12A shows a first side of the sensor pouch. FIG. 12B shows a second (opposite) side of the sensor patch. FIG. 12C shows a side-view cross-section of the sensor patch. FIG. 12D shows a top-view cross-section of the sensor patch.

Sensor patch 1200 is adapted to fit onto and conform to the convex shape of an outer wall of a concrete test cylinder. In particular, patch 1200 includes a side 1215 having a concave shape. A plurality of holes 1223 are disposed on concave side 1215. The inside of sensor patch 1200 includes a volume 1240.

Figure 13A:
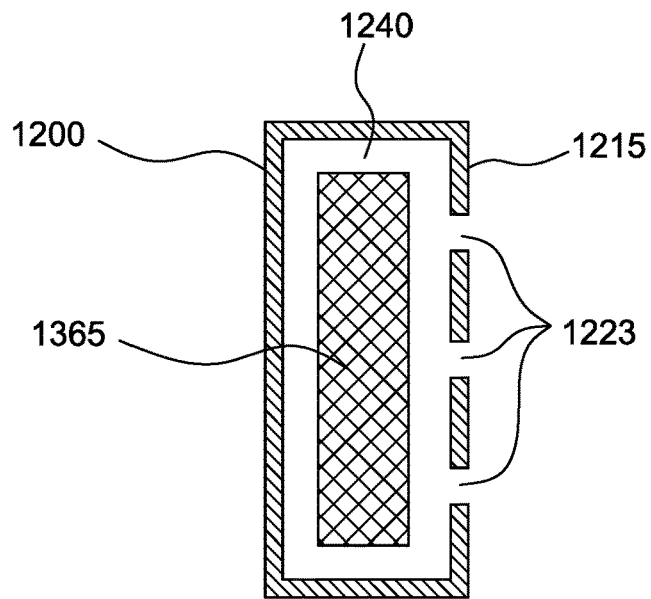
FIGS. 13A-13B show a temperature sensor within a sensor pouch in accordance with an embodiment.
Figure 13B:
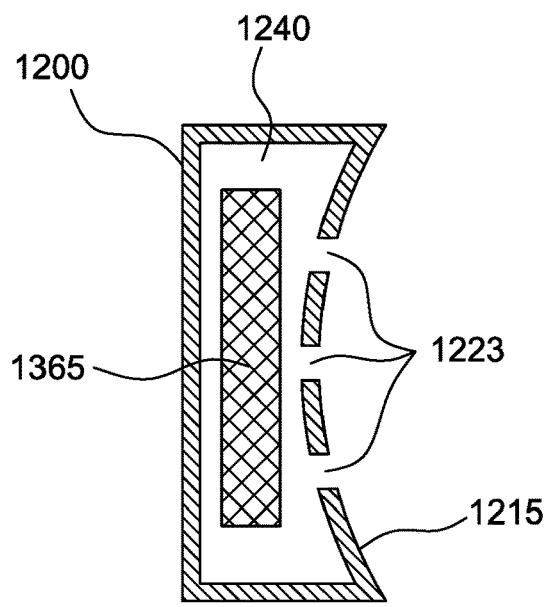

In accordance with FIGS. 13A-13B, a temperature sensor 1365 is placed into sensor patch 1200. Specifically, temperature sensor 1365 is disposed within volume 1240 inside sensor patch 1200. In one embodiment, one side of sensor patch 1200 may be removed (by screws, etc.) to facilitate the placement of a temperature sensor therein.

Thus, in some embodiments, a sensor patch may include a housing (which includes the various sides of the sensor patch such as side 1215 in FIG. 12C), and a cavity (such as volume 1240) defined within the housing. A temperature sensor and/or other sensors, transmitters, etc. may be disposed within the cavity.

Figure 14A:
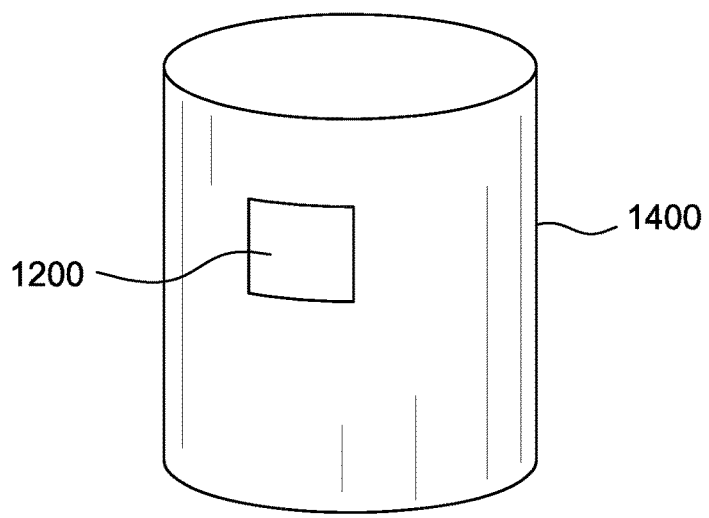
FIG. 14A shows a sensor pouch attached to an outer surface of a concrete test cylinder in accordance with an embodiment.

In accordance with an embodiment, sensor patch 1200 is attached to the side of a concrete test cylinder. FIG. 14A shows sensor patch 1200 attached to an outer surface of a concrete test cylinder 1400.

Figure 14B:
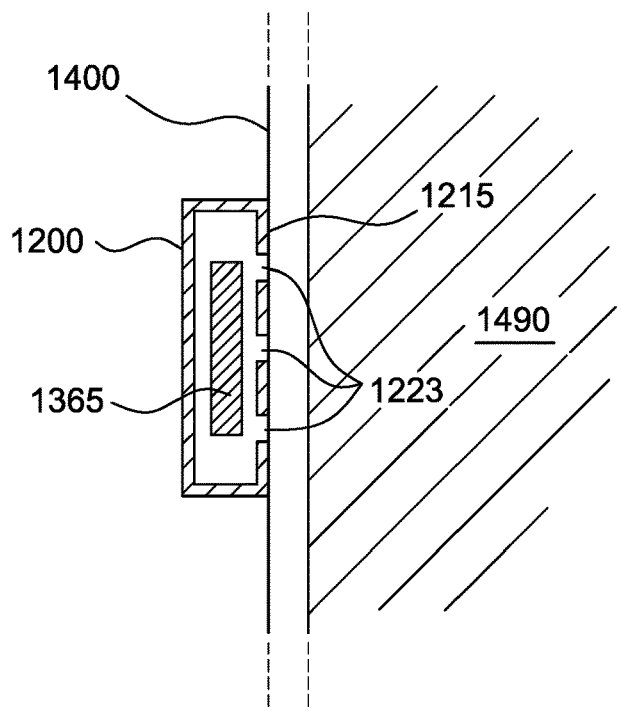
FIG. 14B shows a cross-section of a sensor pouch and of a concrete test cylinder in accordance with an embodiment.

FIG. 14B shows a cross-section of sensor patch 1200 and of concrete test cylinder 1400 in accordance with an embodiment. Concrete test cylinder 1400 holds a concrete mixture 1490. Concave side 1215 of sensor patch 1200 is in contact with or proximate to an outer surface of test cylinder 1400. Holes 1223 allow heat from test cylinder 1400 to penetrate into sensor patch 1200, enabling temperature sensor 1365 to obtain temperature measurements.

After concrete is poured into concrete test cylinder 1400, temperature sensor 1365 begins to obtain temperature measurements. In a manner similar to those discussed above, temperature measurements may be transmitted to a remote device and used to generate a prediction of a performance characteristic for the concrete 1490 in test cylinder 1400.

Figure 15:
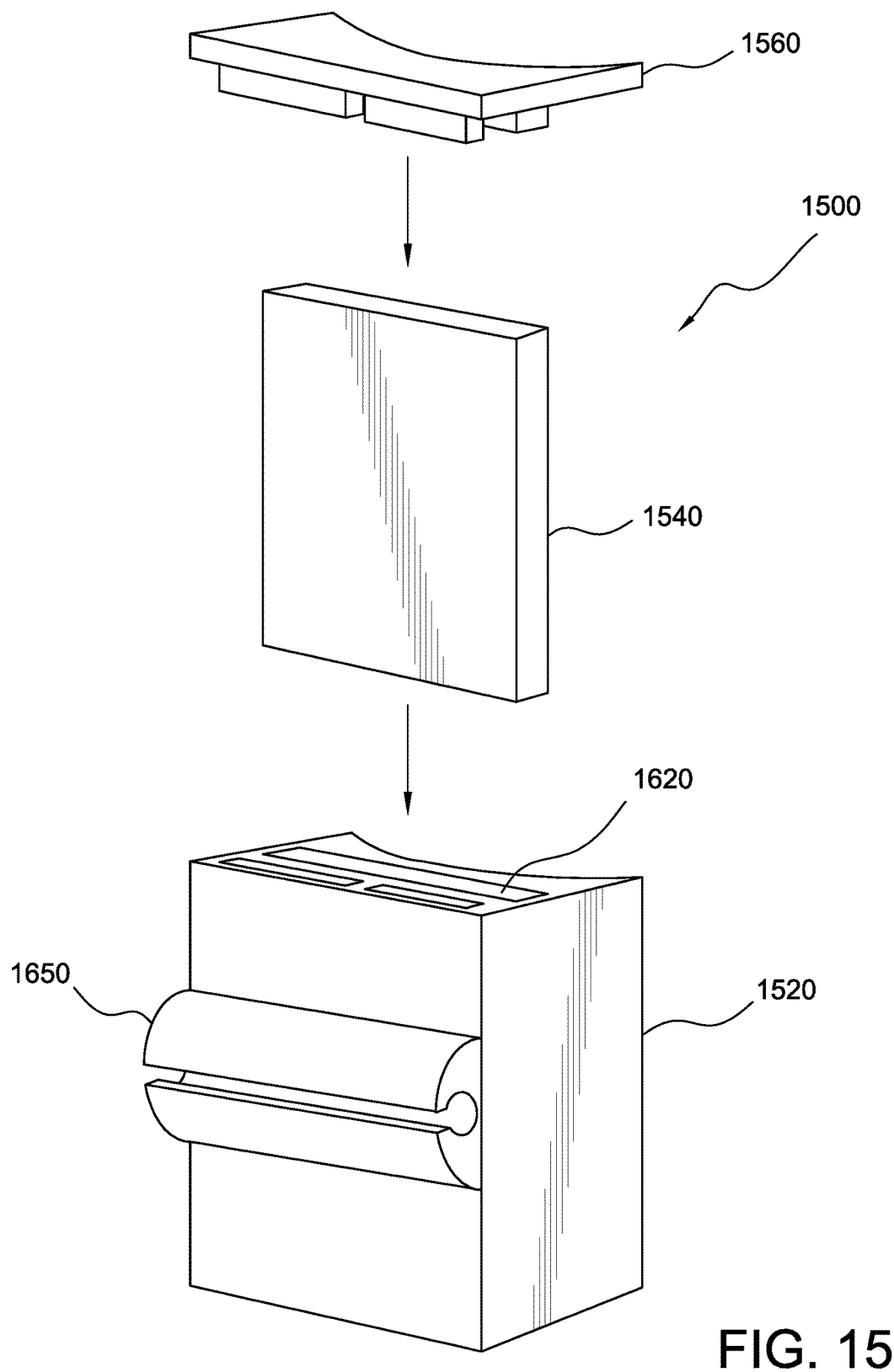
FIG. 15 shows components of a sensor patch 1500 in accordance with another embodiment.

FIG. 15 shows components of a sensor patch 1500 in accordance with another embodiment. Sensor patch 1500 includes a sensor enclosure body 1520, a sensor device 1540, and a cover 1560. Sensor device 1540 is adapted to fit into an opening 1620 of sensor enclosure body 1520. Cover 1560 fits onto an end of sensor enclosure body 1520. When in place on sensor enclosure body 1520, cover 1560 covers and protects sensor device 1540.

Figure 16A:
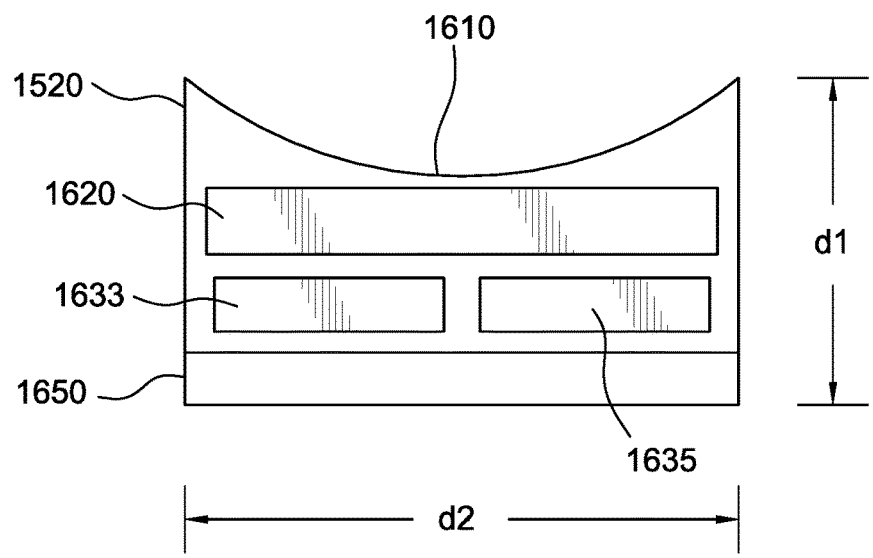
FIG. 16A shows a top view of a sensor pouch in accordance with an embodiment.
Figure 16B:
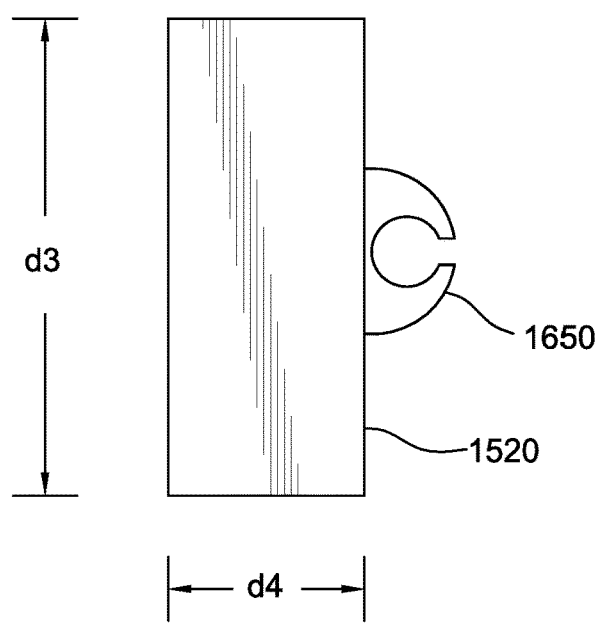
FIG. 16B shows a side view of the sensor patch of FIG. 16A.
Figure 16C:
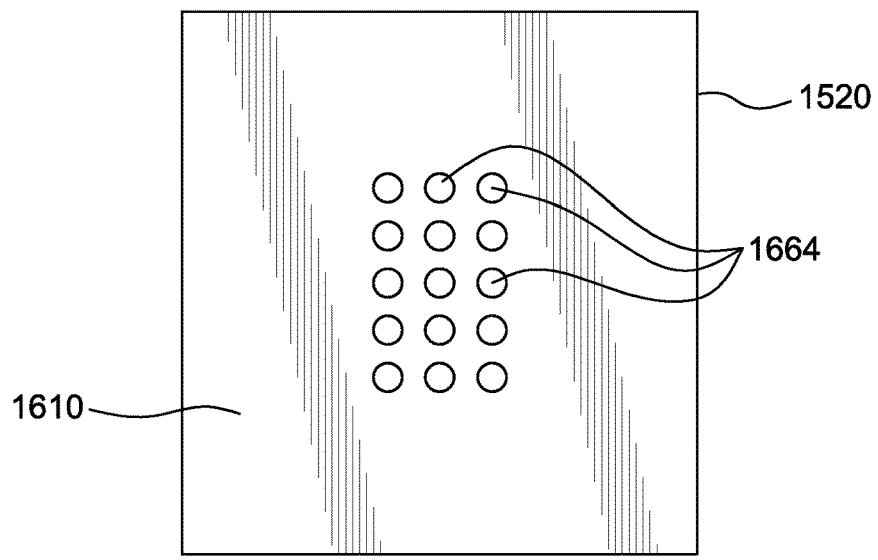
FIG. 16C shows a front view of the sensor patch of FIG. 16A.
Figure 16D:
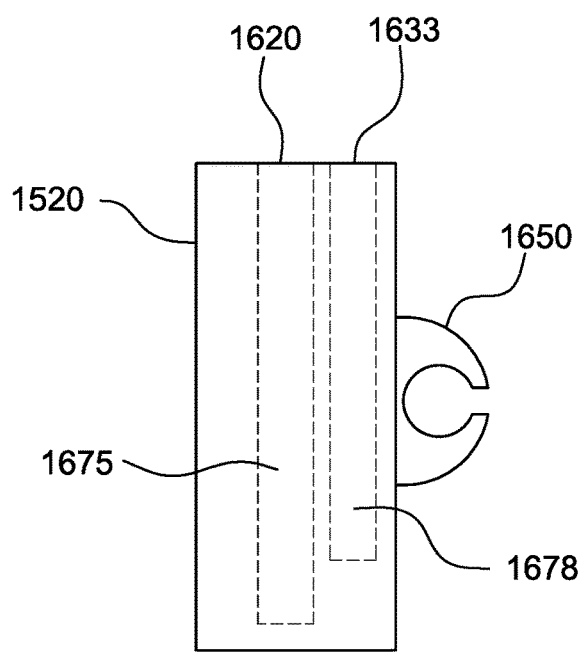
FIG. 16D shows a side view cross-section of the sensor patch of FIG. 16A.

FIGS. 16A-16D show a sensor patch in accordance with an embodiment. FIG. 16A shows a top view of the sensor pouch. FIG. 16B shows a side view of the sensor patch. FIG. 16C shows a front view of the sensor patch. FIG. 16D shows a side view cross-section of the sensor patch.

Referring to FIG. 16A, sensor enclosure body 1520 includes opening 1620, an opening 1633, and an opening 1635. Opening 1620 is adapted to receive and hold sensor device 1540. Sensor enclosure body 1520 has a side 1610 having a concave shape. Side 1610 of sensor enclosure body 1520 is adapted to fit onto and conform to the convex shape of an outer wall of a concrete test cylinder. Sensor enclosure body 1520 has a first dimension d1 which may be, for example, between 0.5-1.5 inches, most preferably 1.08 inches. Sensor enclosure body 1520 has a second dimension d2 which may be, for example, between 1.5-2.0 inches, most preferably 1.72 inches.

Referring to FIG. 16B, sensor enclosure body 1520 includes a connector 1650 disposed along the side of its structure opposite concave side 1610. In one embodiment, the sensor patch is positioned against the outside surface of a cylinder that contains concrete. Connector 1650 is adapted to receive an element that holds the sensor patch in place. For example, connector 1650 may be an opening adapted to receive a cable, band, ring, etc. Alternatively, connector 1650 may be a hook, or other type of connector. For example, connector 1650 may hold a portion of a band or ring (e.g., a portion of an O-ring that circles a cylinder). For example, a band or ring may exert pressure to press the sensor patch against the cylinder, or may hold the sensor patch in place in another manner. Sensor enclosure body 1520 has a third dimension d3 which may be, for example, between 1.5 and 2.0 inches, most preferably 1.71 inches. Sensor enclosure body 1520 has a fourth dimension d4 which may be, for example, between 1.5 and 2.0 inches, most preferably 0.77 inches.

Referring to FIG. 16C, sensor enclosure body 1520 also includes a plurality of holes 1664 disposed on concave side 1610. Holes 1664 allow air to pass between the interior of sensor enclosure body 1520 to the exterior of sensor enclosure body 1520.

Referring to FIG. 16D, sensor enclosure body 1520 includes an internal volume 1675 accessible via opening 1620. Volume 1675 is adapted to hold sensor device 1540. Sensor enclosure body 1520 also includes a volume 1678 accessible via opening 1633.

Figure 17A:
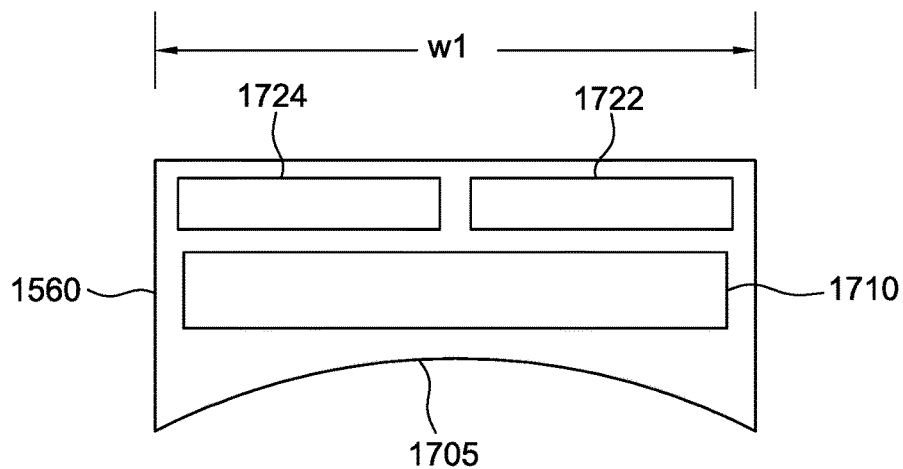
FIG. 17A shows a bottom view of a cover in accordance with an embodiment.
Figure 17B:
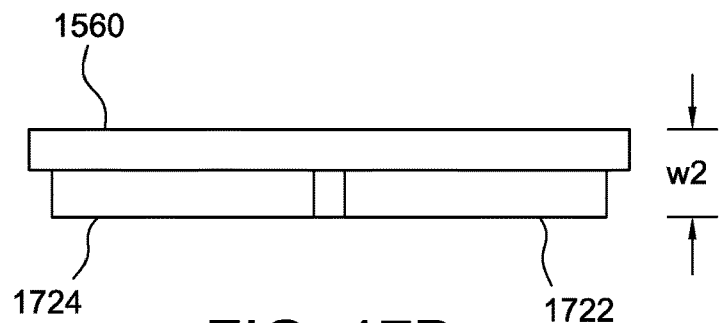
FIG. 17B shows a first side view of the cover of FIG. 17A.
Figure 17C:
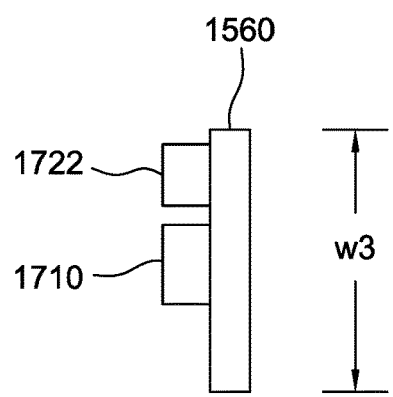
FIG. 17C shows a second side view of the cover of FIG. 17A.

FIGS. 17A-17C show cover 1560 in accordance with an embodiment. FIG. 17A shows a bottom view of cover 1560. FIG. 17B shows a first side view of cover 1560. FIG. 17C shows a second side view of cover 1560.

Referring to FIG. 17A, cover 1560 includes a first tab 1710 adapted to fit into opening 1620, a second tab 1722 adapted to fit into opening 1635, and a third tab 1724 adapted to fit into opening 1633. Cover 1560 has a first dimension w1, which may be between 1.5-2.0 inches, most preferably 1.72 inches.

Referring to FIG. 17B, cover 1560 has a second dimension w2, which may be between 0.1-0.5 inches, most preferably 0.24 inches. Referring to FIG. 17C, cover 1560 has a third dimension w3, which may be between 0.5-1.0 inches, most preferably 0.77 inches.

Figure 18:
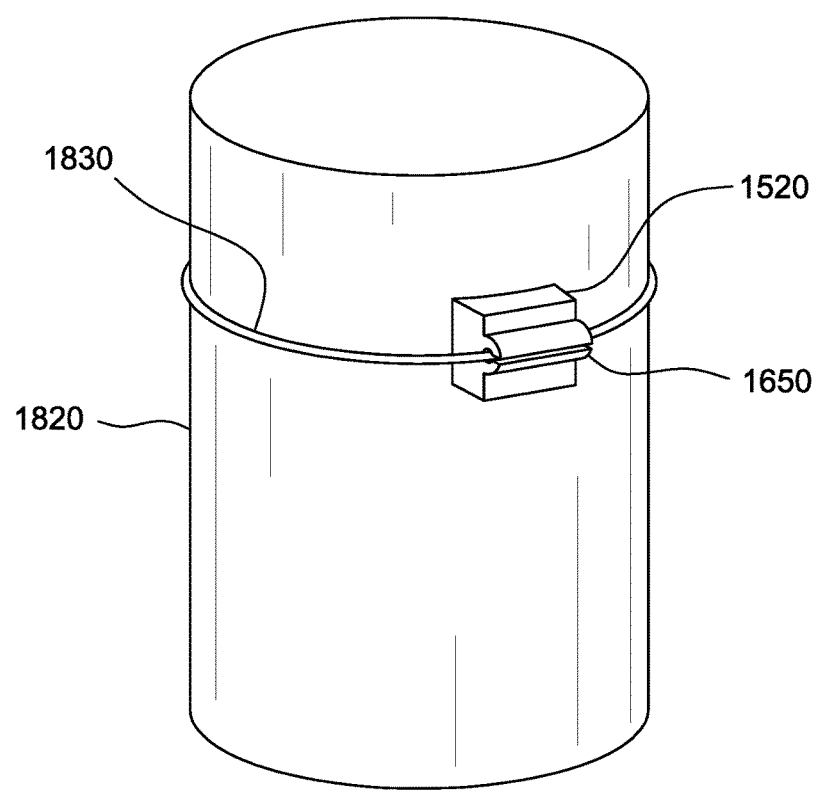
FIG. 18 shows a sensor patch attached to a side of a test cylinder in accordance with an embodiment.

FIG. 18 shows a sensor patch (including sensor enclosure body 1520) attached to the side of a test cylinder in accordance with an embodiment. Specifically, sensor enclosure body 1520 is attached to the surface of a side of a test cylinder 1820 by a ring 1830 that passes through connector 1650. Ring 1830 is sufficiently tight to hold sensor enclosure body 1520 in place against the surface of test cylinder 1820.

It has been observed that when a test cylinder and a sensor patch are used outdoors to test a specimen of concrete, the sensors within the sensor patch may be affected (e.g., heated) by solar radiation and other environmental factors, thereby causing measurements to be unreliable or inaccurate. There is a need for systems and methods to ensure that measurements made by sensors in a sensor patch are reliable and accurate under varying environmental conditions.

Figure 19:
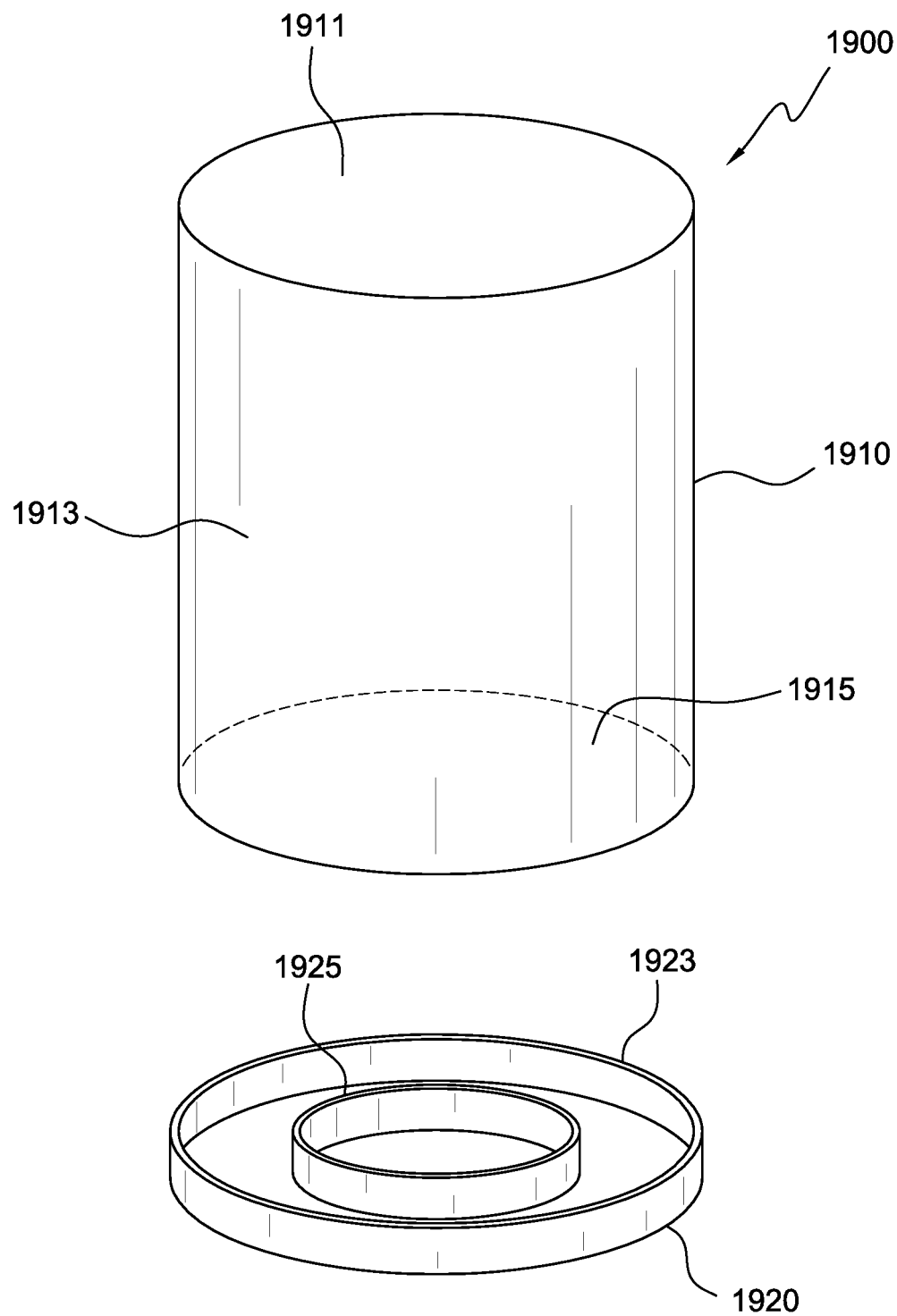
FIG. 19 shows a cylinder enclosure system in accordance with an embodiment.

FIG. 19 shows a cylinder enclosure system in accordance with an embodiment. Enclosure system 1900 includes a cover 1910 and a base 1920. Cover 1910 is a hollow cylinder having a closed top portion 1911 and a round side portion 1913, and an open bottom 1915. Base 1920 has an outer ring 1923 and an inner ring 1925. Cover 1910 is adapted to fit into outer ring 1923.

Figure 20:
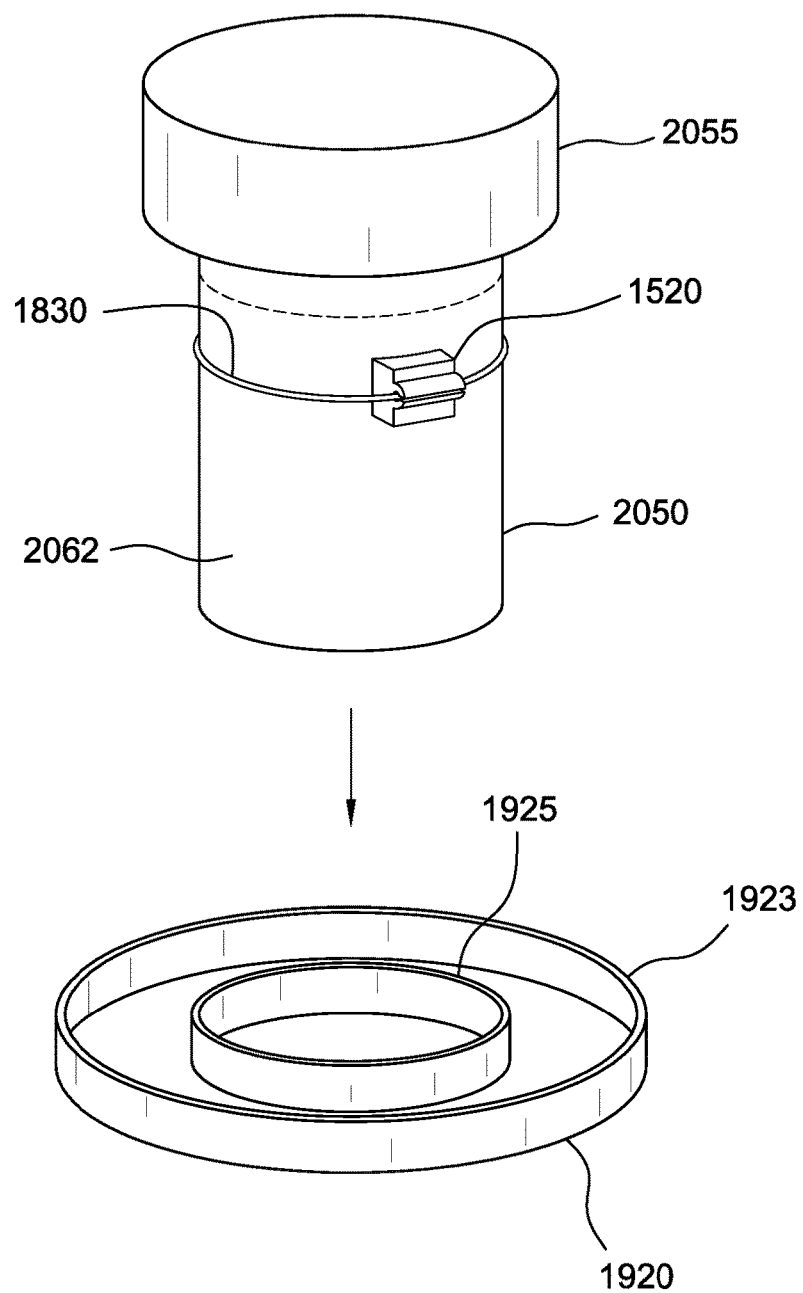
FIGS. 20-22 illustrate a method of placing a test cylinder in a cylinder enclosure system in accordance with an embodiment.

In one embodiment shown in FIG. 20, inner ring 1925 of base 1920 is adapted to receive and hold a standard test cylinder. Therefore, in one embodiment, inner ring 1925 has a diameter of 4 inches and is adapted to receive a 4×8 test cylinder. In another embodiment, inner ring 1925 has a diameter of 6 inches and is adapted to receive a 6×12 test cylinder. Cover 1910 is adapted to cover and enclose a standard test cylinder. Accordingly, in one embodiment, cover 1910 is adapted to cover and enclose a 4×8 test cylinder. For example, cover 1910 may have dimensions of 6×12 inches, sufficient to cover a 4×8 test cylinder. Other dimensions may be used.

In another embodiment, cover 1910 is adapted to cover and enclose a 6×12 test cylinder. For example, cover 1910 may have dimensions of 9×18 inches, sufficient to cover a 6×12 test cylinder. Other dimensions may be used.

In one embodiment, cover 1910 and base 1920 are made from a plastic material. Other materials may be used. In one embodiment, the surface of cover 1900 includes a reflective material, such as foil, reflective paint, reflective sprayed material, etc. Cover 1900 may have a light-colored surface, such as white or silver.

Figure 21:
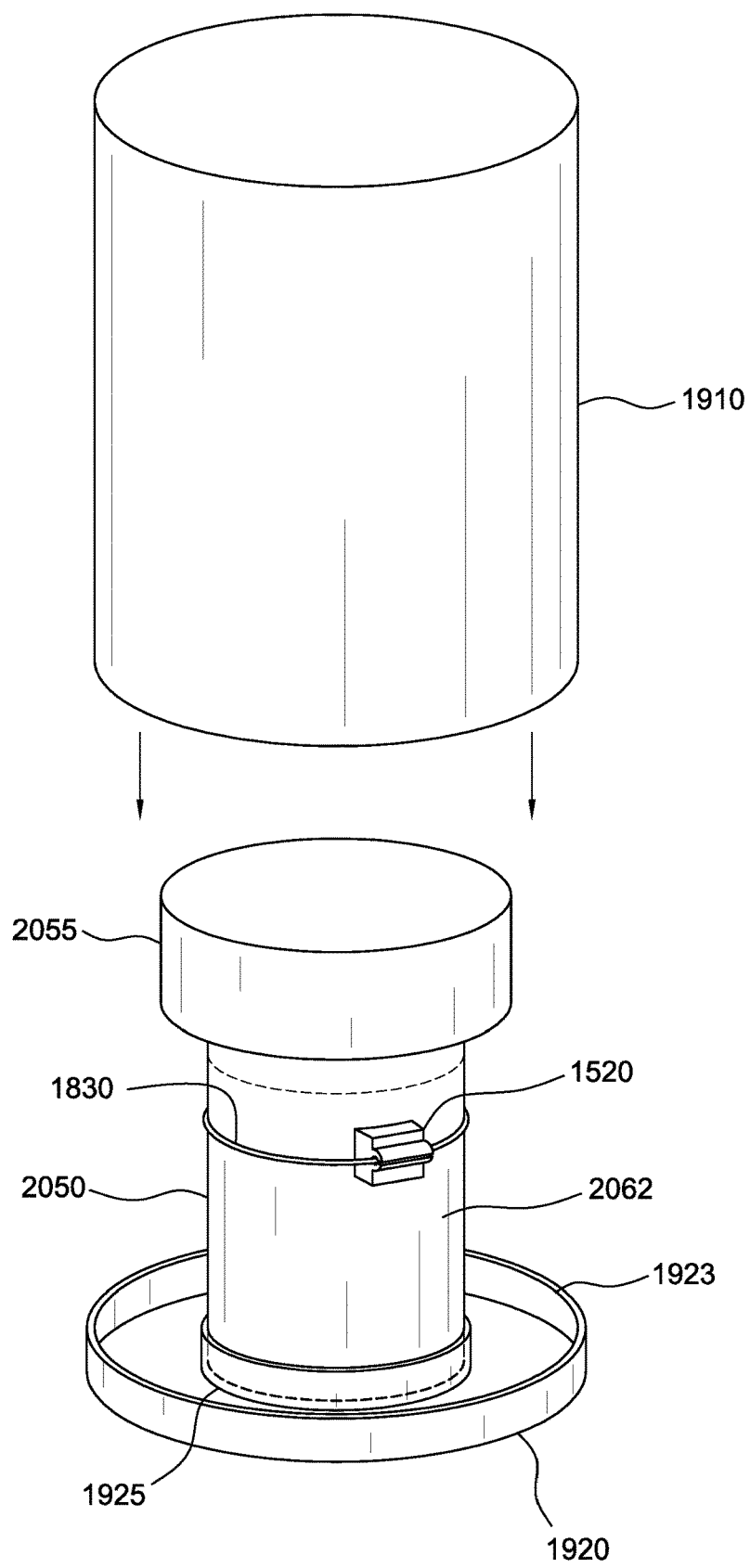
Figure 22:
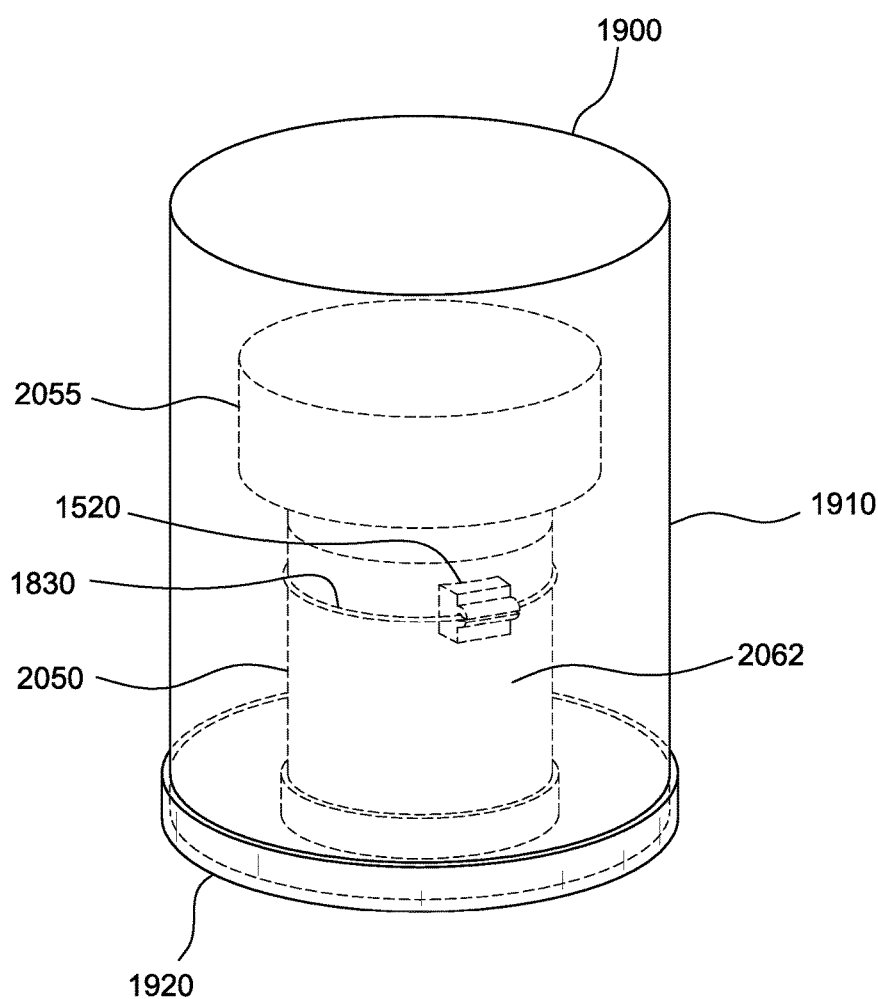

In one embodiment, a standard test cylinder is placed in cylinder enclosure system 1900. FIGS. 20-22 illustrate a method of placing a test cylinder into cylinder enclosure system 1900 in accordance with an embodiment. Referring to FIG. 20, a test cylinder 2050, including a cap 2055 and a sensor patch (illustrated by sensor enclosure body 1520) containing a sensor device, and which holds a specimen of concrete 2062, is placed into inner ring 1925 of base 1920. Referring to FIG. 21, cover 1910 is placed over cylinder 2050 and cap 2055, and fits into outer ring 1923 of base 1920.

Referring to FIG. 22, test cylinder 2050 (with cap 2655 and sensor enclosure body 1520) may remain within cylinder enclosure system 1900 as long as desired. For example, after a specimen of concrete is poured into test cylinder 2050 for the purpose of testing the concrete, the test cylinder may be placed into cylinder enclosure system 1900. The cylinder enclosure system 1900 (with the test cylinder 2050 and sensor enclosure body 1520 inside) may then be placed outdoors for the duration of the test, for example. Advantageously, even in direct sunlight, cylinder enclosure system 1900 protects cylinder 2050, sensor enclosure body 1520, and the specimen of concrete 2062, from the effects of solar radiation and other environmental factors.

Figure 23:
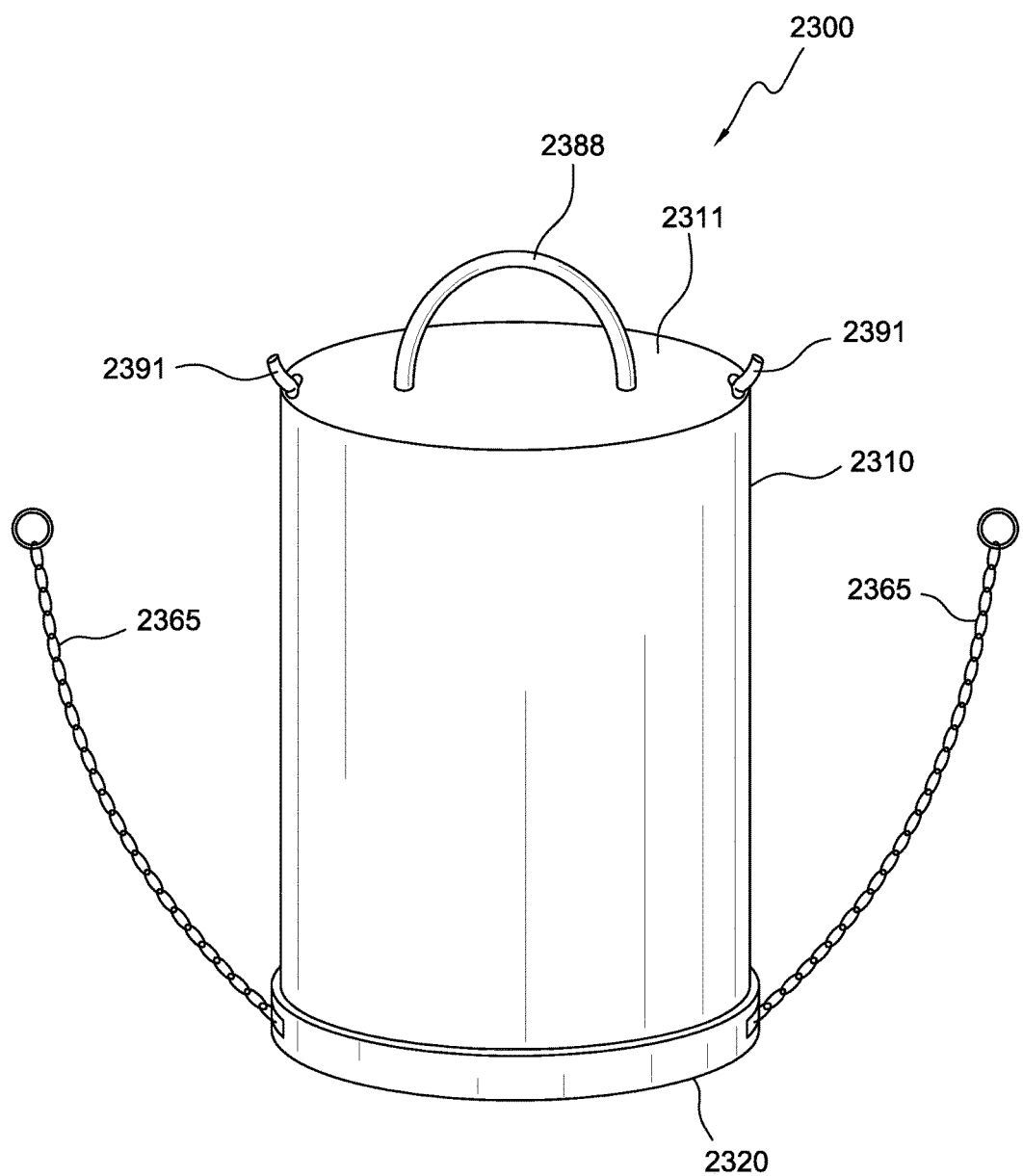
FIG. 23 shows a cylinder enclosure system in accordance with an embodiment.

FIG. 23 shows a cylinder enclosure system in accordance with another embodiment. System 2300 includes a cover 2310 and a base 2320. A handle 2388 is attached to a top surface 2311 of cover 2310. Two hooks 2391 are attached at the edges of top surface 2311 of cover 2310. Two chains 2365 are attached to base 2320.

Figure 24:
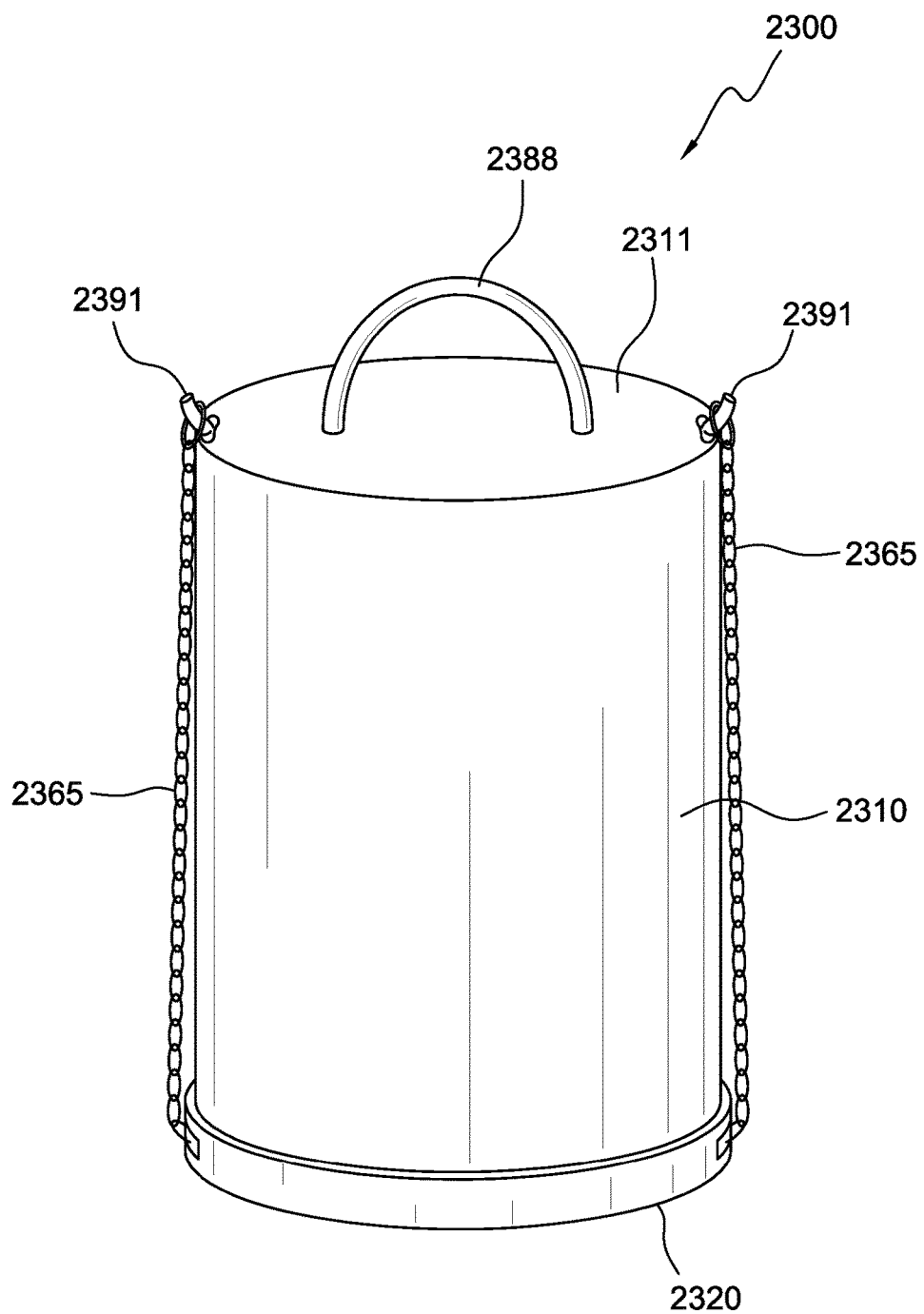
FIG. 24 shows a cylinder enclosure system in accordance with an embodiment.

In accordance with an embodiment, after a test cylinder is placed into cylinder enclosure system 2300, in the manner described herein, cover 2310 is placed onto base 2320, and chains 2365 are drawn up and attached to hooks 2391 on cover 2310, as shown in FIG. 24. The chains secure cover 2310 on base 2320. Once secured, cylinder enclosure system 2300 may be easily picked up by handles 2388 and transported from one location to a second location.

In accordance with other embodiments, a cylinder enclosure system may be closed and secured using other techniques and mechanisms. For example, the base of a cylinder enclosure system may contain a first set of threads (internal or external), and the cover of the cylinder enclosure system may contain a second set of threads adapted to engage with the first set of threads. Accordingly, the cover may be secured to the base by placed the threads together in a well-known manner and turning the cover so that the first threads engage with the second threads.

In accordance with another embodiment, a first test cylinder containing a concrete mixture is placed in a first cylinder enclosure system. A second test cylinder containing an inert substance having thermal characteristics similar to the concrete mixture is placed in a second cylinder enclosure system. For example the inert substance may include copper, or dry concrete, or another substance. The first and second cylinder enclosure systems (with their respective test cylinders) are placed in a selected environment (such as at a selected field location at a construction site) for a predetermined period of time. Temperature measurements are obtained from both test cylinders at selected times while the concrete mixture in the first test cylinder dries. A first temperature profile associated with the concrete mixture and a second temperature measurement associated with the substance in the second test cylinder are determined based on the temperature measurements. One or more characteristics of the concrete mixture may be determined by comparing the first and second temperature profiles. For example, a heat maximum associated with the heat of hydration generated by the concrete mixture may be observed by subtracting the second temperature profile from the first temperature profile. Other characteristics of the concrete mixture may be determined in a similar manner.

In another embodiment, other mechanisms may be used to place a sensor on a concrete test cylinder, and the test cylinder may then be placed within a cylinder enclosure system such as cylinder enclosure system 2300. For example, a sensor or sensor device may be placed in different location or a different position on or proximate a concrete test cylinder, and then the cylinder may be placed in a cylinder enclosure system. For example, in one embodiment, a cap is placed on a concrete test cylinder that holds a concrete mixture. The cap may cover and seal the top of the test cylinder, for example. One or more sensors such as a temperature sensor, a humidity sensor, etc., are attached to the cap. For example, one or more sensors may be disposed on an internal surface of the cap proximate the concrete mixture. The concrete test cylinder with the cap is placed in a cylinder enclosure system. While the test cylinder and cap are in the cylinder enclosure system, the sensor(s) obtain temperature measurements, humidity measurements, etc., and may transmit the data. A remote processor may receive the measurement data and determine a characteristic of the concrete mixture based on the data, as described herein.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A system comprising:
 a cylinder having a diameter of at least four (4) inches, the cylinder being adapted to hold concrete;
 a ring that defines 360 degrees and encircles an outer side of the cylinder, the ring having a diameter of at least four (4) inches; and
 a sensing device disposed on the outer side of the cylinder and attached to the ring, the sensing device comprising:
  a concave side adapted to conform to a curvature of the outer side of the cylinder;
  a second side opposite the concave side;
  an internal volume adapted to hold one or more sensor elements; and
  a sensor element removably disposed within the internal volume of the sensing device, the sensor element comprising a temperature sensor adapted to obtain temperature measurements; and
  a connector disposed on the second side of the sensing device, the connector having a hole adapted to receive the ring.

2. The system of claim 1, further comprising:
 a transmitter adapted to transmit the temperature measurements to a second device.

3. The system of claim 1, further comprising:
 a humidity sensor;
 a capillary needle disposed on the concave side;
 wherein the humidity sensor connects via the capillary needle to moisture in the concrete.

4. The system of claim 3, wherein the capillary needle has a length substantially equal to a thickness of a side of the cylinder.

5. The system of claim 1, wherein the sensor element further comprises:
 a humidity sensor; and
 a transmitter adapted to transmit the temperature measurements to a second device.

6. The system of claim 5, wherein the concave side further comprises a plurality of holes adapted to allow heat to pass between an external environment of the system and the internal volume.

* * * * *